United States Patent [19]
Bernstein et al.

[11] Patent Number: 5,179,112
[45] Date of Patent: Jan. 12, 1993

[54] HETEROCYCLIC AMIDE DERIVATIVES AND PHARMACEUTICAL USE

[75] Inventors: Peter R. Bernstein, Wallingford, Pa.; Frederick J. Brown, Newark, Del.; Victor G. Matassa, Wilmington, Del.; Ying K. Yee, Kennett Square, Pa.

[73] Assignee: ICI Americas Inc., Wilmington, Del.

[21] Appl. No.: 711,478

[22] Filed: Jun. 6, 1991

Related U.S. Application Data

[62] Division of Ser. No. 380,059, Jul. 14, 1989, Pat. No. 5,030,043, which is a division of Ser. No. 852,798, Apr. 16, 1986, Pat. No. 4,859,692.

[30] Foreign Application Priority Data

Apr. 17, 1985 [GB] United Kingdom ............... 8509882
Oct. 17, 1985 [GB] United Kingdom ............... 8525658

[51] Int. Cl.$^5$ .............. A61K 31/41; A61K 31/415; C07D 231/56; C07D 249/18
[52] U.S. Cl. .................... 514/359; 514/381; 514/382; 514/394; 514/405; 514/407; 514/443; 514/469; 548/253; 548/261; 548/304.4; 548/361.5; 548/304.7; 549/57; 549/467
[58] Field of Search .............. 548/253, 261, 325, 359, 548/372; 549/57, 467; 514/359, 381, 382, 394, 405, 407, 443, 469

[56] References Cited

U.S. PATENT DOCUMENTS

| | | | |
|---|---|---|---|
| 2,381,935 | 8/1945 | Strain | 260/241 |
| 3,271,416 | 9/1966 | Shen et al. | 548/494 |
| 3,470,298 | 9/1969 | Palazzo | 514/407 |
| 4,499,299 | 2/1985 | Bernstein et al. | 514/570 |
| 4,859,692 | 8/1989 | Bernstein et al. | 514/381 |
| 5,030,643 | 7/1991 | Bernstein et al. | 514/373 |

FOREIGN PATENT DOCUMENTS

| | | |
|---|---|---|
| 671445 | 4/1966 | Belgium . |
| 738727 | 9/1969 | Belgium . |
| 0166591 | 1/1986 | European Pat. Off. . |
| 2854987 | 6/1980 | Fed. Rep. of Germany . |
| 4.035M | 3/1966 | France . |
| 2004453 | 11/1969 | France . |
| 7.631M | 1/1970 | France . |
| 1050302 | 12/1966 | United Kingdom . |

OTHER PUBLICATIONS

*Chemical Abstracts*, 74 4635m, 1971.
Cook, J. A., Wise, W. C., and Halushka, P. V., "Protective Effect of a Selective Leukotriene Antagonist in Endotoxemia in the Rat", *The Journal of Pharmacology and Experimental Therapeutics*, vol. 235, No. 2., pp. 470–474 (1985).
Denzlinger, C., Rapp, S., Hagmann, W. and Keppler, D., "Leukotrienes as Mediators in Tissue Trauma", *Science*, vol. 230, pp. 330–332 (1985).
European Patent Search Report for Corresponding European Patent Application No. 86302850.2 (1988).
Fleisch, Jerome H., Rinkema, Lynn E., Haisch, Klaus D., Swanson-Bean, Dorothy, Goodson, Theodore, Ho, Peter P. K., and Marshall, Winston S., "LY171883, 1-[2-Hydroxy-3-Propyl-4-[4-(1H-Tetrazol-5-yl)-Butoxy]Phenyl]Ethanone, and Orally Active Leukotriene D$_4$ Antagonist[1]", *The Journal of Pharmacology an Experimental Therapeutics*, vol. 233, No. 1, pp. 148–157 (1985).
Hannig, E., Kollmorgen, Chr. and Dressel, M., "Zur Kenntnis einiger Derivate des 1-Benzyl-6-aminoindazols", *Pharmazie* 29, H. 10–11 (1974), pp. 685–686.
Krell, Robert D., "Pharmacologic Characterization of Isolated Rhesus Monkey Bronchial Smooth Muscle", *The Journal of Pharmacology and Experimental Therapeutics*, vol. 211, No. 2, pp. 436–443 (1979).
Marx, Jean L., "Leukotrienes in Allergy and Inflammation", *Science*, vol. 215, Mar. 12, 1982, pp. 1380–1382.

*Primary Examiner*—Richard L. Raymond
*Attorney, Agent, or Firm*—Rosemary M. Miano; Thomas E. Jackson

[57] ABSTRACT

The invention concerns novel, pharmaceutically useful, amide derivatives of certain benzoheterocyclylalkanoic acids (and related tetrazoles and acylsulphonamides) of the formula I and salts thereof, wherein the radicals $R^1$, $R^2$, L, X, Y, Z, $A^1$, Q, $A^2$ and M have the meanings set out in the specification. The invention also includes pharmaceutical compositions incorporating a formula I compound or a salt thereof, a process for the manufacture of the said compound, together with intermediates for use in the latter process.

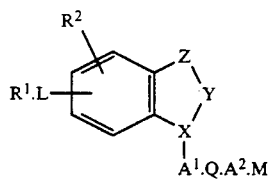

15 Claims, No Drawings

HETEROCYCLIC AMIDE DERIVATIVES AND PHARMACEUTICAL USE

This is a divisional application of co-pending application Ser. No. 07/380,059 filed on Jul. 14, 1989, now U.S. Pat. No. 5,030,043, which application is a divisional application of Ser. No. 06/852,798 filed on Apr. 16, 1986 and now U.S. Pat. No. 4,859,692.

SUMMARY AND BACKGROUND OF THE INVENTION

This invention concerns novel heterocyclic amide derivatives and, more particularly, novel amides derived from benzoheterocyclylalkanoic acids (and related tetrazoles and acylsulphonamides), which antagonise the pharmacological actions of one or more of the arachidonic acid metabolites known as leukotrienes (hereafter referred to as "leukotriene antagonist properties"). The novel derivatives are useful whenever such antagonism is desired. Thus, such compounds may be of value in the treatment of those diseases in which leukotrienes are implicated, for example in the treatment of allergic or inflammatory diseases, or of endotoxic or traumatic shock conditions. The invention also provides pharmaceutical compositions containing the novel derivatives for use in such treatments, and processes and intermediates for the manufacture of the novel derivatives.

In U.S. Pat. Nos. 3,271,416 and 3,470,298 there are described 5-acetamido-1-benzylalpha,2-dimethylindole-3-acetic acid derivatives and (5-acetamido-1-benzyl-1H-indazol-3-yl)oxyacetic acid derivatives, respectively, as antiinflammatory compounds N-acyl derivatives of 6-amino-1-benzylindazole have been described (see E. Hannig, et al., *Pharmazie*, (1974), 29:685-7): and 6-(acetylamino)-2,3-dihydro-4H-1,4-benzoxazine-4-propanoic acid methyl ester has been registered (Chemical Abstracts Registry Number 27802-53-5) *Chem. Abs.* 74:4635(M). We have now discovered a series of benzoheterocyclic derivatives which have an amidic substituent in the benzenoid ring and which unexpectedly possess the property of antagonising one or more of the arachidonic acid metabolites known as leukotrienes and this is the basis for our invention.

DESCRIPTION OF THE INVENTION

According to the invention there is provided a compound of the formula I

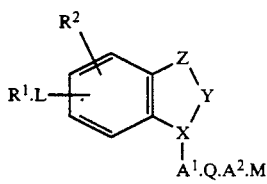

wherein the group $>X-Y-Z-$ is selected from the group consisting of:

(a) $>CRc-CRaRb-NRd-$
(b) $>C=N-Za-$
(c) $>C=CRa-Zb-$
(d) $>N-CRa=N-$
(e) $>N-CRbRe-CRcRf-Zb-$
(f) $>N-N=N-$
(g) $>N-NRg-CO-$
(h) $>N-N=C.ORd-$ in which ">"indicates two separate bonds, Ra is hydrogen or (1-4C)alkyl;

Rb and Rc are each hydrogen or, together with the existing carbon to carbon bond, form an unsaturated linkage:

Rd is hydrogen or (1-10C)alkyl optionally containing one or two double or triple bonds and in which a carbon atom may optionally be replaced by oxygen or sulphur, said (1-10C)alkyl additionally optionally bearing a substituent selected from the group consisting of (1-4C)alkoxy, cyano, carboxy, 1H-tetrazol-5-yl, carbamoyl, N-(1-4C)carbamoyl, N,N-di(1-4C)alkyl]carbamoyl, and (1-4C)alkoxycarbonyl, or Rd is (3-8C)cycloalkyl, (3-8C)cycloalkyl-(1-4C)alkyl, (2-6C)alkanoyl or phenyl-(1-4C)alkyl, the phenyl moiety of which optionally bears a substituent selected from the group consisting of cyano, halogeno, (1-4C)alkyl, (1-4C)alkoxy and trifluoromethyl:

Re and Rf are independently hydrogen or (1-4C)alkyl;

Rg is (1-4C)alkyl;

Za is oxy, thio, or substituted imino of the formula $-N(Rd)-$ in which Rd has any of the meanings defined above;

Zb is oxy or thio;

the group $R^1.L-$ stands for amidic radicals of the formula: $R^1.W.CO.NH-$ or $R^1.W$ CS.NH—, in which $R^1$ is (2-10C)alkyl optionally containing 1 or more fluorine substituents: or $R^1$ is phenyl-(1-6C)alkyl in which the (1-6C)alkyl moiety may optionally bear a fluoro or (1-4C)alkoxy substituent and in which the phenyl moiety may optionally bear a substituent selected from the group consisting of halogeno, (1-4C)alkyl, (1-4C)alkoxy and trifluoromethyl: or $R^1$ is (3-8C)cycloalkyl or (3-8C)cycloalkyl-(1-6C)alkyl, the cyclic moiety of any of which optionally may contain one unsaturated linkage and may optionally bear 1 or 2 (1-4C)alkyl substituents;

W is oxy, thio, imino or a direct link to $R^1$;

$R^2$ is hydrogen, halogeno, (1-4C)alkyl or (1-4C)alkoxy:

Q is phenylene optionally bearing 1 or more substituents independently selected from the group consisting of halogen, hydroxy, (1-4C)alkyl, (1-4C) alkoxy and trifluoromethyl;

$A^1$ is (1-2C)alkylene or vinylene:

$A^2$ is methylene; vinylene or a direct link to M; and

M is an acidic group selected from the group consisting of carboxy, an acylsulphonamide residue of the formula $-CO.NH.SO_mR^3$ and 1H-tetrazol-5-yl in which m is the integer 1 or 2 and $R^3$ is (1-6C)alkyl, (3-8C)-cycloalkyl, (6-12C)aryl, heteroaryl comprising 5-12 atoms at least one of which is carbon and at least one of which is selected from oxygen, sulfur, and nitrogen, (6-12C)aryl-(1-4C)alkyl, in any of which the aromatic or heteroaromatic moiety may bear 1 or 2 substituents selected from the group consisting of halogeno, (1-4C)alkyl, (1-4C)alkoxy, trifluoromethyl, nitro and amino;

or a pharmaceutically acceptable salt thereof.

It will be appreciated that certain of the compounds of formula I, for example those wherein $R^1$ contains an asymmetrically substituted carbon atom, may exist in, and be isolated in, optically-active and racemic forms. In addition, it will be appreciated that certain compounds of formula I, for example, those wherein Rd or the linkage $-A^1.Q.A^2-$ contains a vinylene group, may exist in, and be isolated in, separate stereoisomeric forms ('E' and 'Z') about that group. Some compounds may exist in more than one tautomeric form. Some compounds may exhibit polymorphism. It is to be understood that the present invention encompasses any racemic, optically-active, tautomeric, polymorphic or stereoisomeric form, or mixtures thereof, which form possesses leukotriene antagonist properties, it being well known in the art how to prepare optically-active forms (for example, by resolution of the racemic form or by synthesis from optically-active starting materials) and to prepare individual 'E' and 'Z' stereoisomers (for example, by chromatographic separation of a mixture thereof) and how to determine the leukotriene antagonist properties by the standard tests described hereinafter.

In this specification Ra, Rb, Rc et cetera stand for generic radicals and have no other significance. It is to be understood that the generic term (1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, "alkylene" and "alkenylene" et cetera.

Particular values for the generic radicals described as ranges above under Ra, Rb, Rc et cetera are as follows:

A particular value for Ra, Re, Rf, Rg or $R^2$ when it is (1–4C)alkyl is, for example, methyl, ethyl or propyl.

A particular value for $R^2$ when it is (1–4C) alkoxy is, for example, methoxy or ethoxy; and when it is halogeno is, for example, fluoro, chloro or bromo.

A particular value for Rd when it is (1–10C)alkyl is, for example, methyl, ethyl, propyl, isopropyl, butyl, isobutyl, sec-butyl, 3-methylbutyl, pentyl or hexyl when it is alkyl containing 1 or 2 double or triple bonds is, for example, vinyl, allyl, 1-propenyl, 2-methylallyl, 3-methylbut-2-enyl, 1,3-pentadienyl, 2-propynyl or 3-butynyl; and when it is alkyl in which one or two carbon atoms are replaced by oxygen or sulphur a particular value is, for example, 2-methoxyethyl or 2-methylthioethyl.

A particular value for an optional substituent on Rd is, for example:

for (1–4C)alkoxy, methoxy or ethoxy;

for N-(1–4C)-alkylcarbamoyl, N-methyl- or N-ethylcarbamoyl;

for N,N-di(1–4C)alkylcarbamoyl, N,N-dimethylcarbamoyl:

for (1–4C)alkoxycarbonyl, methoxycarbonyl, ethoxycarbonyl, or t-butoxycarbonyl.

A particular value for Rd when it is (3–8C) cycloalkyl is, for example, cyclopropyl, cyclopentyl or cyclohexyl: when it is (3–8C)cycloalkyl-(1–4C)alkyl a particular value is, for example, cyclopropylmethyl, cyclopentylmethyl or cyclohexylmethyl; when it is (2–6C)alkanoyl a particular value is, for example, acetyl or propionyl: and when it is phenyl-(1–4C)alkyl a particular value is, for example, benzyl, 1-phenylethyl or 2-phenylethyl.

A particular value for $R^1$ when it is (2–10C)alkyl is, for example, ethyl, propyl, isopropyl, butyl, isobutyl, sec-butyl, t-butyl, pentyl, 1-ethylpropyl, hexyl, heptyl, 1-ethylpentyl or nonyl; and when it contains 1 or more fluorine substituents a particular value is, for example, 2,2,2-trifluoroethyl or heptafluoropropyl.

Particular values for $R^1$ when it is phenyl-(1–6C)alkyl include, for example, benzyl, 1-phenylethyl, 2-phenylethyl, 1-phenylpropyl, 2-phenylpropyl, 3-phenylpropyl, 1-methyl-1-phenylethyl, 1-phenylbutyl and 1-phenylpentyl; and a particular value for an optional (1–4C)alkoxy substituent on the (1–6C)alkyl moiety is, for example, methoxy or ethoxy.

Particular values for certain optional substituents which may be present on a phenyl moiety of $R^1$ or Rd, or as a part thereof, as defined above, include, for example:

for halogen: a member selected from the group consisting of fluoro, chloro and bromo;

for (1–4C)alkyl: a member selected from the group consisting of methyl and ethyl: and for (1–4C)alkoxy: a member selected from the group consisting of methoxy and ethoxy.

A particular value for $R^1$ when it is (3–8C) cycloalkyl is, for example, cyclopropyl, cyclobutyl, cyclopentyl, cyclohexyl or cycloheptyl; when it is (3–8C)cycloalkyl-(1–6C)alkyl a particular value is, for example, cyclobutylmethyl, cyclopentylmethyl, cyclohexylmethyl, 1-cyclopentylethyl, 2-cyclopentylethyl, 1-cyclopentylpropyl, 1-cyclohexylpropyl, 1-cyclopentylbutyl, 1-cyclohexylbutyl; and a particular value for a radical containing an unsaturated linkage in the cycloalkyl ring is, for example, cyclohexenyl or cyclohexenyl-(1–6C)alkyl (such as cyclohexenylmethyl or 1-(cyclohexenyl)-butyl); and a particular value for an optional (1–4C)alkyl substituent on the cyclic moiety of such a radical is, for example, methyl, ethyl or isopropyl.

A particular value for Q is m-phenylene or p-phenylene, preferably bearing a fluoro, chloro, (1–4C)alkyl, (1–4C)alkoxy or trifluoromethyl substituent.

A particular value for $A^1$ when it is (1–2C)-alkylene is, for example, methylene, ethylene or ethylidene.

A particular value for $R^3$ when it is (1–6C)-alkyl is, for example, methyl, ethyl, propyl, isopropyl or butyl; when it is (3–8C)cycloalkyl a particular value is, for example, cyclopentyl or cyclohexyl; when it is (6–12C)aryl a particular value is, for example, phenyl, 1-naphthyl or 2-naphthyl; when it is heteroaryl a particular value is, for example, furyl, thienyl or pyridyl; and when it is (6–12C)aryl-(1–4C)alkyl a particular value is, for example, benzyl, 1-naphthylmethyl or 2-naphthylmethyl.

Particular values for optional substituents which may be present on an aromatic or heteroaromatic moiety of $R^3$, or on a part thereof, include those defined above in connection with a phenyl moiety in $R^1$.

More particular values for the groups listed above include by way of example those selected from the groups consisting of:

for $R^1$: ethyl, propyl, isopropyl, butyl, isobutyl, sec-butyl, t-butyl, pentyl, 1-ethylpropyl, hexyl, heptyl, 1-ethylpentyl, nonyl, heptafluoropropyl, benzyl, 4-chlorobenzyl, 4-trifluoromethylbenzyl, 4-methylbenzyl, 1-phenylethyl, 2-phenylethyl, 1-methyl-1-phenylethyl, 1-phenylpropyl, 1-phenylpentyl, alpha-fluorobenzyl, alpha-methoxybenzyl, cyclobutyl, cyclopentyl, cyclohexyl, cyclopentylmethyl, cyclohexylmethyl, 2-cyclopentylethyl, 1-cyclopentylbutyl, 1-cyclohexylpropyl, 1-cyclohexylbutyl, 5-methyl-2-(1-methylethyl)cyclohexyl, and 1-cyclohexen-4-yl;

for $R^2$: hydrogen, fluoro, chloro, bromo, methyl and methoxy;

for R³: methyl, isopropyl, butyl, cyclopentyl, phenyl, 4-chlorophenyl, 4-methylphenyl, 2-methylphenyl, naphthyl, thien-2-yl and 6-chloropyrid-3-yl;

for Ra: hydrogen and methyl;

for Rb and Rc: hydrogen, Rb and Rc together with the existing carbon to carbon bond form an unsaturated linkage:

for Rd: hydrogen, methyl, ethyl, propyl, butyl, pentyl, hexyl, allyl, propargyl, 3-methylbutyl, 3-methylbut-2-enyl, 2-carbamoylethyl, carboxymethyl, carboxyethyl, N-ethylcarbamoylmethyl, N,N-dimethylcarbamoylmethyl, 2-carboxyvinyl, 2-(methoxycarbonyl)vinyl, 2-methoxyethyl, 3-methoxypropyl, cyclopentyl, cyclopropylmethyl, acetyl, benzyl, 3-cyanobenzyl and 4-chlorobenzyl:

for Re and Rf: hydrogen, methyl and ethyl:

for Rg: methyl, ethyl, and propyl:

for A¹: methylene and ethylene:

for A²: a direct linkage and methylene;

for Q: m-phenylene and p-phenylene (optionally bearing a fluoro, chloro, hydroxy, methyl, methoxy or trifluoromethyl substituent); and for W: oxy, imino, thio and a direct linkage.

Examples of specific groups which are of special interest include those selected from the groups consisting of:

for R¹: butyl, pentyl, 1-ethylpentyl, 1-phenylpropyl, alpha-fluorobenzyl, alpha-methoxybenzyl, cyclopentyl, and cyclopentylmethyl;

for R²: hydrogen;

for R³: phenyl and 2-methylphenyl;

for Ra: hydrogen;

for Rb and Rc: hydrogen, and Rb and Rc together with the existing carbon to carbon bond form an unsaturated linkage;

for Rd: hydrogen, methyl, ethyl, propyl, hexyl, allyl, propargyl, 3-methylbutyl, 3-methylbut-2-enyl, carboxymethyl, carboxyethyl, N-ethylcarbamoylmethyl, N,N-dimethylcarbamoylmethyl, 2-methoxyethyl, cyclopentyl, cyclopropylmethyl, acetyl, benzyl, and 3-cyanobenzyl;

for Re or Rf: hydrogen;

for Rg: propyl;

for A¹: methylene;

for A²: a direct linkage:

for Q: m-phenylene and p-phenylene (optionally bearing an hydroxy or methoxy substituent); and for W: oxy, imino and a direct linkage.

It will be appreciated that within the above definitions there are included a number of sub-groups of compounds, for example:

(i) indoles and indolines of formula Ia;

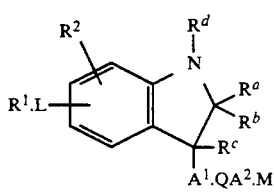

(ii) benzisoxazoles, benzisothiazoles and indazoles of formula Ib;

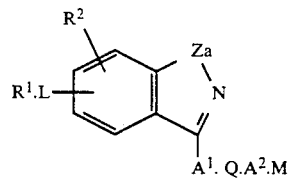

(iii) benzo[b]furans and benzo[b]thiophenes for formula Ic;

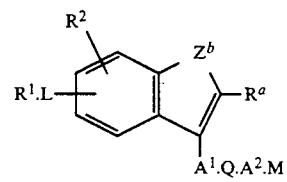

(iv) benzimidazoles for formula Id:

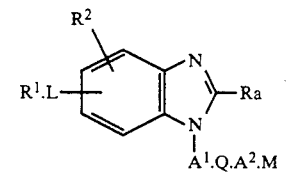

(v) 1,4-benzoxazines and 1,4-benzothiazines for formula Ie;

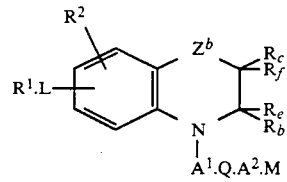

(vi) benzotriazoles of formula If:

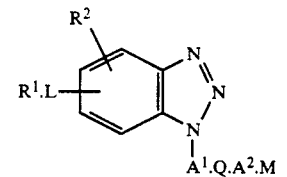

(vii) indazolones of formula Ig; and

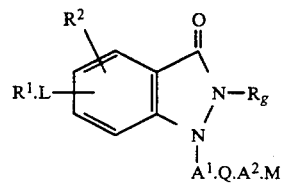

(viii) indazoles of formula Ih;

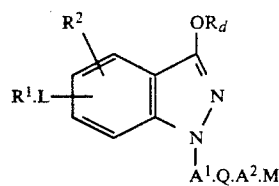

and wherein, in each sub-group, m, $R^1-R^3$, Ra–Rg, Za, Zb, $A^1$, $A^2$, Q, W and M have any of the above defined meanings; together with the pharmaceutically acceptable salts thereof.

Within the above sub-groups yet further sub-groups of compounds of the invention comprise the following:

(ix) those compounds of formula Ia wherein Rb and Rc, together with the existing carbon to carbon bond, form an unsaturated linkage;

(x) those compounds of formula Ie wherein Zb is oxy or thio, and Rb and Rc are hydrogen;

and wherein, in each sub-group (ix) and (x) the remaining generic radicals have any of the above defined meanings; together with the pharmaceutically acceptable salts thereof.

In the above sub-groups a preferred value for $A^1$ is, for example, methylene; a preferred value for $A^2$ is, for example, a direct link to M; a preferred value for Q is, for example, p-phenylene (optionally substituted with methoxy, especially methoxy in the ortho-position relative to $A^1$); and a preferred value for M is carboxy, 1H-tetrazol-5-yl or a radical of the formula —CO.NH.SO$_2$R$^4$ wherein $R^4$ is phenyl, optionally substituted as defined above for $R^3$, for example, 2-methylphenyl. In general, it is preferred for the group $R^1$.L— to be attached to the benzene moiety of formula I in such a way that it bears a meta-relationship to the group X but does not bear an ortho-relationship to the group Z. A preferred value for $R^1$.L— is, for example, $R^1$.W.CO.NH—; a preferred value for W is, for example, oxy, imino or a direct linkage; a preferred value for $R^1$ when W is oxy or imino is, for example, cyclopentyl; and a preferred value for $R^1$ when W is a direct linkage is, for example, cyclopentylmethyl.

Preferred groups of compounds of the invention comprise the indole derivatives of the following formula IIa,

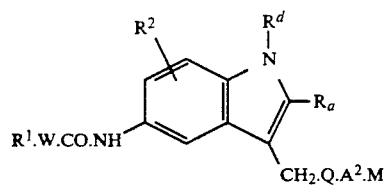

the indazole derivatives of the following formula IIb,

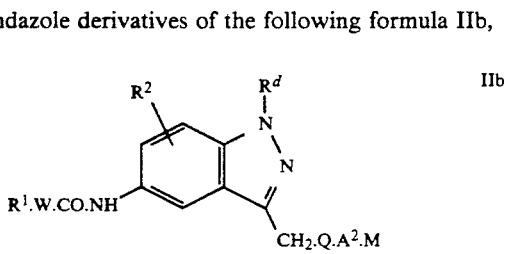

the benzo[b]thiophene derivatives of the following formula IIc,

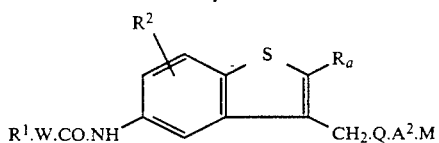

the benzimidazole derivatives of the following formula IId,

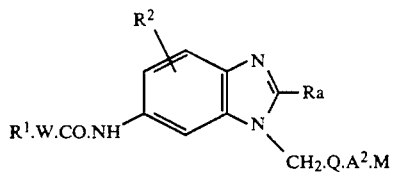

the 2,3-dihydrobenz-1,4-oxazine derivatives of the following formula IIe,

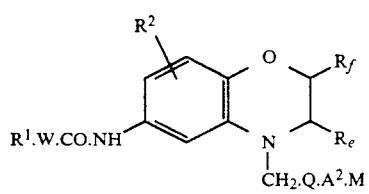

the benzotriazole derivatives of the following formula IIf,

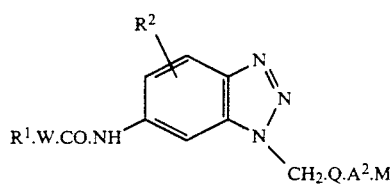

and the indazole derivatives of the following formula IIg,

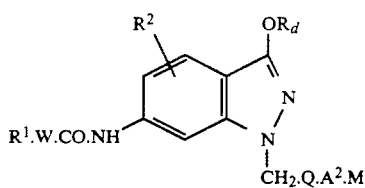

wherein $R^1$, $R^2$, Ra, Rd, Re, Rf, W, Q, $A^2$ and M have any of the meanings defined hereinbefore; together with the pharmaceutically acceptable salts thereof. Particularly preferred values of Rd for the derivatives of formula IIa and IIb when M is carboxy include methyl, propyl, 2-methoxyethyl, N-ethylcarbamoylmethyl, and cyclopentyl. Particularly preferred values of Rd for the derivatives IIa and IIb when M is a radical of the formula —CO.NH.SO$_2$R$^4$ wherein $R^4$ is phenyl include hydrogen, methyl, 2-methoxyethyl and N-ethylcarbamoylmethyl. Particularly preferred values of Rd for the derivatives IIa and IIb when M is a radical of the formula —CO.NH.SO$_2$R$^4$ wherein $R^4$ is 2-methylphenyl include methyl and N,N-dimethylcarbamoylmethyl. For the derivatives IIg when $R^1$.L— is $R^1$.W.CO.NH— wherein $R^1.W-$ is cyclopentyloxy and M is carboxy or $-CO.NH.SO_2R^4$ wherein $R^4$ is phenyl, a particularly preferred value of Rd is methyl. For the derivatives IIg when $R^1.L-$ is $R^1$ W.CO.NH— wherein $R^1$ is cyclopentylmethyl and W is a direct linkage and M is carboxy or $-CO.NH.SO_2R^4$ wherein $R^4$ is 2-methylphenyl, a particularly preferred value of Rd is N-ethylcarbamoylmethyl.

Specific compounds of the invention are described in the accompanying examples. However, of these the compounds N-[4-[5-(cyclopentyloxycarbonyl)amino-1-methylindol-3-ylmethyl]-3-methoxybenzoyl]benzenesulphonamide, N-[4-[5-(cyclopentyloxycarbonyl)amino-1-(N-ethylcarbamoylmethyl)indol-3-ylmethyl]-3-methoxybenzoyl]benzenesulphonamide, N-4-[5-(cyclopentyloxycarbonyl)amino-1-methylindazol-3-ylmethyl]-3-methoxybenzoyl]benzenesulphonamide, N-[4-[5-(cyclopentyloxycarbonyl)amino-1-methylindol-3-ylmethyl-3-methoxybenzoyl]-2-methylbenzenesulphonamide, N-[4-[5-(2-cyclopentylacetamido)-1-(N,N-dimethylcarbamoylmethyl)indol-3-ylmethyl]-3-methoxybenzoyl]-2-methylbenzenesulphonamide, N-4-[6-(cyclopentyloxycarbonyl)amino-2,3-dihydrobenz-1,4-oxazin-4-ylmethyl]-3-methoxybenzoyl]benzenesulphonamide, N-4-[6-(2-cyclopentylacetamido)-2,3-dihydrobenz-1,4-oxazin-4-ylmethyl]-3-methoxybenzoyl]benzenesulphonamide, N-[4-[5-(cyclopentyloxycarbonyl)aminobenzo[b]thien-3-ylmethyl-3-methoxybenzoyl]benzenesulphonamide, N-[4-[6-(2-cyclopentylacetamido)benzimidazol-1-ylmethyl]-3-methoxybenzoyl]benzenesulphonamide, N-[4-[6-(2-cyclopentylacetamido)-2,3-dihydrobenz-1,4-oxazin-4-ylmethyl-3-methoxybenzoyl]-2-methylbenzenesulphonamide, N-[4-[6-(cyclopentyloxycarbonyl)amino-3-methoxyindazol-1-ylmethyl]-3-methoxybenzoyl]benzenesulphonamide, N-[4-[5-(N'-cyclopentylureido)-1-methylindol-3-ylmethyl]-3-methoxybenzoyl]-2-methylbenzenesulphonamide, N-[4-[6-(2-cyclopentylacetamido)benzotriazol-1-ylmethyl]-3-methoxybenzoyl]benzenesulphonamide, N-[4-[5-(cyclopentyloxycarbonyl)aminoindol-3-ylmethyl]-3-methoxybenzoyl]benzenesulphonamide, N-[4-[5-(cyclopentyloxycarbonyl)amino-1-(2-methoxyethyl)indol-3-ylmethyl]-3-methoxybenzoyl]-benzenesulphonamide, N-[4-[5-(2-cyclopentylacetamido)-1-methylindol-3-ylmethyl]-3-methoxybenzoyl]benzenesulphonamide, N-[4-[6-(2-cyclopentylacetamido)-3-(N-ethylcarbamoylmethoxy)indazol-1-ylmethyl]-3-methoxybenzoyl]-2-methylbenzenesulphonamide, and N-[4-[6-(cyclopentyloxycarbonyl)aminobenzimidazol-1-ylmethyl]-3-methoxybenzoyl]-benzenesulphonamide are particularly preferred and may be used either in the free acid form or as their corresponding pharmaceutically acceptable salts.

Examples of suitable pharmaceutically acceptable salts are salts formed with bases which form a physiologically acceptable cation, such as alkali metal (especially sodium and potassium), alkaline earth metal (especially calcium and magnesium), aluminum and ammonium salts, as well as salts made with appropriate organic bases such as triethylamine, morpholine, piperidine and triethanolamine. For those compounds of formula I which are sufficiently basic, examples of suitable pharmaceutically acceptable salts include acid-addition salts such as those made with a strong acid, for example hydrochloric, sulphuric or phosphoric acid.

The compounds of formula I may be made by processes well known in the chemical art for the production of structurally analogous heterocyclic compounds. Such processes for the manufacture of a compound of formula I as defined above are provided as further features of the invention and are illustrated by the following procedures in which the meanings of generic radicals are as defined above, T is defined as a group selected from the group consisting of COORh (wherein Rh has the values defined below), CN, and the values defined above for M; U is defined as a suitable leaving group, for example, halogeno (especially chloro, bromo, or iodo) or alkane- or arene-sulphonyloxy (especially methanesulphonyloxy or p-toluenesulphonyloxy); and Hal is defined as halogeno, especially chloro, bromo or iodo.

(A) For those compounds wherein M is a carboxylic acid group, decomposing a suitable ester of formula III

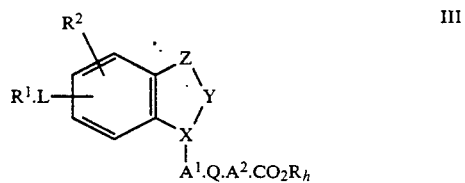

wherein Rh is a conveniently removed acid protecting group, for example, (1–6C)alkyl optionally bearing an acetoxy, (1–4C)alkoxy or (1–4C)alkylthio substituent, or is phenyl or benzyl.

A particular value for Rh is, for example, methyl, ethyl, propyl, t-butyl, acetoxymethyl, methoxymethyl, 2-methoxyethyl, methylthiomethyl, or phenyl or benzyl.

Certain of the starting esters of formula III may be active in their own right as leukotriene antagonists (such as, for example, by in vivo conversion to the corresponding carboxylic acid), for example, those wherein Rh is (1–6C)alkyl, and these are included within the scope of the invention.

It will be appreciated that the decomposition can be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Also, when Rh is methyl, the ester may be decomposed by nucleophilic demethylation with, for example, lithium thioethoxide in N,N'-dimethylpropyleneurea. Alternatively, it may in certain circumstances, for example, when Rh is t-butyl, be possible to carry out the decomposition by thermal means, for example, by heating the ester of formula III at a temperature of, for example, 100°–150° C., alone or in a suitable solvent or diluent such as diphenylether. In addition, when Rh is t-butyl the decomposition may be performed, for example, by using trimethylsilyl triflate and then water, in a conventional manner. Still further, in certain circumstances, for example, when Rh is benzyl, it may be possible to carry out the decomposition by reductive means, for example, by the use of hydrogen at about atmospheric pressure in the presence of a suitable catalyst, such as palladium or platinum, conveniently on charcoal as a support.

A preferred method for decomposing an ester of formula III comprises reacting the ester with a suitable base, for example, an alkali or alkaline earth metal hydroxide or carbonate (such as lithium hydroxide, potassium hydroxide, sodium hydroxide, calcium hydroxide or potassium carbonate) in a suitable, aqueous solvent or diluent, for example, water, optionally together with a water-miscible alkanol, glycol, ketone or ether (such as methanol, ethanol, ethylene glycol, 2-methoxyethanol, acetone, methyl ethyl ketone, tetrahydrofuran or 1,2-dimethoxyethane), at a temperature of, for example, 15°-100° C. and conveniently at or near ambient temperature. When such a method is employed, the resultant carboxylic acid of formula I, wherein M is a carboxy group, is initially obtained as the corresponding salt of the base used for the hydrolysis and may be isolated as such or converted to the free acid form by a conventional acidification procedure, for example, by reaction with a suitable strong acid such as hydrochloric or sulphuric acid.

(B) Acylating an amine of the formula IV,

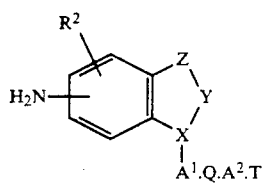

but wherein T is chosen from the values defined for M.

A suitable acylating agent when W is oxy, thio or a direct link is, for example, an acid halide of the formula $R^1.Xa.CO.Hal$ wherein Xa has one of above-mentioned values for W.

A suitable acylating agent when W is imino is, for example, an isocyanate of the formula $R^1.NCO$.

When an acid halide is used as the acylating agent, a suitable base such as triethylamine, N-methylmorpholine, pyridine, 2,6-lutidine or 4-(dimethylamino)pyridine is conveniently also employed, preferably together with a suitable inert solvent or diluent, for example, dichloromethane, diethyl ether, tetrahydrofuran or 1,2-dimethoxyethane. The same or similar inert solvents or diluents may be used when an isocyanate or isothiocyanate is employed as the acylating agent.

When W is a direct link, the acylating agent may also be a carboxylic acid of the formula $R^1.CO_2H$. In which case a suitable condensing agent, for example, a carbodiimide (such as dicyclohexylcarbodiimide or 1-(3-dimethylaminopropyl)-3-ethylcarbodiimide, or a salt thereof) or 1,1'-carbonyldiimidazole, is also employed, preferably together with a suitable inert solvent or diluent, for example, one of those mentioned above for use with an acid halide.

In general, the acylations are carried out at a temperature in the range of, for example, $-20°$ to $60°$ C. and, conveniently, at or near ambient temperature.

(C) For a compound of formula I wherein >X—Y—Z— has the value (a) or (b) as defined hereinabove, but wherein Za is a substituted imino of the formula —N(Rd)—, reacting an imino compound of the formula V,

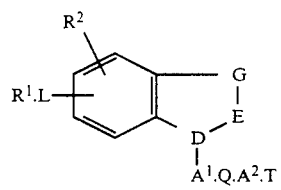

wherein >D—E—G— is a group of the formula >CRc—CRbRa—NH— or >C=N—NH—, but wherein T is chosen from the values defined for M, with an alkylating agent of the formula Rd.U.

This procedure is particularly suitable for the production of, for example, compounds of formula IIa.

The reaction is preferably performed in the presence of a suitable base, for example, an alkali metal hydride such as sodium or potassium hydride in a suitable inert solvent or diluent, for example, tetrahydrofuran, 1,2-dimethoxyethane, N-methylpyrrolidone, or N,N-dimethylformamide. Alternatively, the compound of formula V may be used in the form of its preformed anhydrous alkali metal salt, for example, by prior reaction with a suitable base such as sodium or potassium methoxide, t-butoxide or hydride, or butyl lithium; in which case a wider range of conventional solvents or diluents may be employed for the reaction with the alkylating agent.

In either case, the alkylation is generally performed at a temperature in the range, for example, $-10°$ to $40°$ C. and, conveniently, at or near ambient temperature.

(D) For a compound of formula I wherein >X—Y—Z— has the value (a) defined hereinabove, but wherein Rb and Rc, together with the existing carbon-to-carbon bond, form an unsaturated linkage, reacting an indole of formula VI

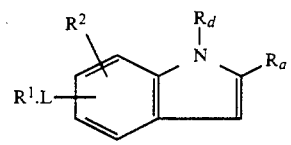

with an alkylating agent of the formula $U.A^1.Q.A^2.M$ in the presence of a suitable Lewis acid.

A particularly suitable Lewis acid is, for example, silver oxide, silver carbonate, silver fluoroborate, silver trifluoroacetate, silver trifluoromethanesulfonate, zinc chloride, ferric chloride or stannic chloride.

The process is generally best performed in a suitable solvent or diluent, for example, in acetone, dichloromethane, acetonitrile or an ether solvent such as 1,2-dimethoxyethane, dioxane or tetrahydrofuran, optionally together with a hydrocarbon diluent such as toluene or xylene, and at a temperature in the range of, for example, 15°-100° C. and, more preferably, in the range 40°-80° C.

(E) For a compound of formula I wherein M is a 1H-tetrazol-5-yl radical, reacting a cyano derivative of formula VII

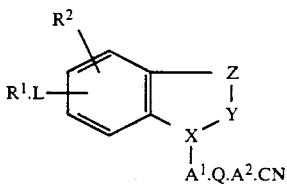

with an azide.

A particularly suitable azide is, for example, an alkali metal azide such as sodium or potassium azide, preferably together with an ammonium halide, for example, ammonium chloride or ammonium bromide or, especially, with triethylammonium chloride. The reaction is preferably performed in a suitable polar solvent, for example, N,N-dimethylformamide or N-methylpyrrolidone, and conveniently at a temperature in the range of, for example, 50° to 160° C.

(F) For a compound of formula I wherein $R^1.L—$ stands for a group of the formula $R^1.Wa.CO.NH—$ or $R^1.Wa.CS.NH—$ in which Wa is oxy, imino or thio, reacting an isocyanate or isothiocyanate of the formula VIII,

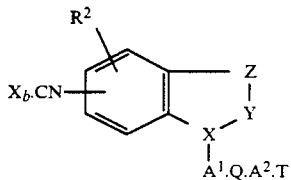

but wherein T is chosen from the values defined for M and wherein Xb is oxygen or sulphur, with the appropriate compound of the formula $R^1.WaH$, for example, an amine of the formula $R^1.NH_2$, an alcohol of the formula $R^1.OH$ or a thiol of the formula $R^1.SH$.

In general, the process is performed at a temperature in the range of, for example, 0°-60° C. and, conveniently in a suitable inert diluent or solvent such as dichloromethane, diethyl ether, methyl t-butyl ether, tetrahydrofuran or dioxane. The starting isocyanate or isothiocyanate of formula VIII may conveniently be obtained by reaction of the corresponding amine of formula IV with phosgene or thiophosgene (or an equivalent reagent, such as trichloromethyl chloroformate for the production of an isocyanate) in a conventional manner.

(G) For a compound of formula I wherein M is a group of the formula $CO.NH.SO_m.R^3$, reacting a compound of formula I wherein M is carboxy (which compound is hereinafter referred to as "acid of formula I") with a sulphonamide derivative of the formula $R^3.SO_m.NH_2$, in the presence of a dehydrating agent.

Thus, for example, a free acid of formula I may be reacted with a suitable dehydrating agent, for example, with dicyclohexylcarbodiimide or 1-(3-dimethylaminopropyl)-3-ethylcarbodiimide, or with a hydrochloride or hydrobromide salt thereof optionally together with an organic base, for example, 4-(dimethylamino)pyridine, in the presence of a suitable solvent or diluent, for example, dichloromethane, at a temperature in the range of, for example, 10° to 50° C., but preferably at or near ambient temperature.

Alternatively, a reactive derivative of an acid of formula I, for example, an acid halide (such as the acid chloride), acid anhydride or a mixed acid anhydride (such as that formed from N,N-diphenylcarbamic acid and the acid of formula I by reaction of the sodium salt of the latter acid with N,N-diphenylcarbamoylpyridinium chloride), may be reacted with an alkali metal salt (such as the lithium, sodium or potassium salt) of the appropriate sulphonamide of the formula $R^4.SO_2.NH_2$, conveniently at or near room temperature and in a suitable solvent or diluent, for example, tetrahydrofuran, N,N-dimethylformamide or dichloromethane.

(H) An alternative process to procedure (D) mentioned above for a compound of formula I, wherein $>X—Y—Z—$ has the value (a) defined above, but wherein Rb and Rc, together with the existing carbon-to-carbon bond, form an unsaturated linkage, reacting an indole of formula VI with an alkylating agent of the formula $U.A^1.Q.A^2.M$.

The process is generally best performed in a suitable solvent or diluent, for example, in a polar solvent (such as N,N-dimethylformamide, N,N'-dimethylpropyleneurea or N-methylpyrrolidone), or in an ether solvent (such as dioxane or 1,2-dimethoxyethane), optionally together with an hydrocarbon diluent such as toluene or xylene.

The alkylation is generally best performed at a temperature in the range, for example 50°-160° C., and, preferably, in the range 70°-100° C.

(I) For a compound of formula I wherein $>X—Y—Z—$ has the value (b) defined hereinabove, but wherein Za is a substituted imino of the formula $—N(Rd)—$, dehydration of an amino-oxime of the formula IX,

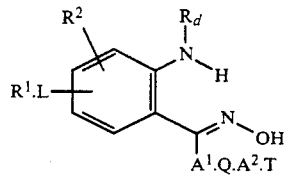

but wherein T is chosen from the values defined for M, by first reacting a compound of formula IX with a suitable condensing agent, for example, a carboxylic acid anhydride (such as acetic or propionic anhydride), preferably together with a suitable solvent or diluent, for example a chlorinated hydrocarbon solvent (such as dichloromethane or dichloroethane) in the presence of an organic base (for example, 4-(dimethylamino)pyridine), followed by heating the resulting O-acyloxime, preferably in the absence of solvent or diluent, but which heating may also be carried out in a suitable inert solvent or diluent, for example, a hydrocarbon solvent (such as toluene or xylene), and at a temperature in the range of 80°-250° C., but preferably in the range of 140°-200° C.

The dehydration of compounds of formula IX may also be carried out without prior derivatization to the acyl derivatives by heating, preferably in the absence of solvent or diluent, but which heating may also be carried out in a suitable solvent or diluent, such as these mentioned above, at a temperature in the range 150°-300° C., but preferably in the range 150°-250° C. Compounds of formula IX, but wherein T is chosen from the values defined for M, may be obtained, by standard procedures known in the art, from compounds of formula X,

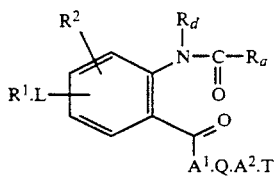

but wherein T is chosen from the values defined for M, such compounds of formula X having been obtained from compounds of formula Ia, wherein Rb and Rc, together with the existing carbon-to-carbon bond, form an unsaturated linkage, by oxidative cleavage of the said unsaturated linkage, using techniques known in the art.

(J) For a compound of formula I, wherein >X—Y—Z— has the value (c) defined above, but wherein Zb is oxy, by dehydration of an hydroxy compound of formula XI,

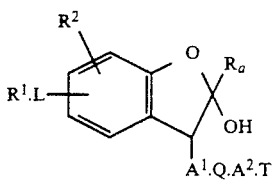

but wherein T is chosen from the values defined for M, for example, by treatment with an acid (such as paratoluenesulphonic acid or hydrochloric acid) in a suitable inert solvent, or diluent, for example a hydrocarbon solvent (such as toluene or xylene), or in an ether solvent (such as dioxane or tetrahydrofuran).

In general, the reaction may be carried out at a temperature in the range of, for example, 50°–150° C., but preferably in the range of 80°–120° C.

Compounds of formula XI may be obtained, by standard oxidative procedures known in the art, from corresponding compounds of formula XII,

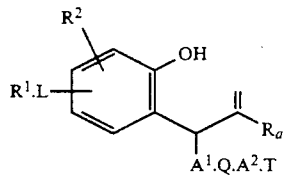

but wherein T is chosen from the values defined for M.

(K) For a compound of formula I, wherein >X—Y—Z— has the value (b) defined hereinabove, but wherein Za is oxy, by dehydration of an hydroxyoxime of formula XIII,

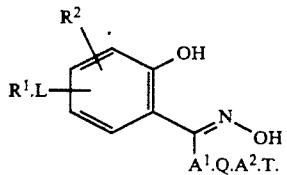

but wherein T is chosen from the values defined for M, by methods similar to those described hereinabove in process (I).

Compounds of formula XIII, wherein T is chosen from the values defined for M, may be obtained, by standard procedures known in the art, from compounds of formula XIV,

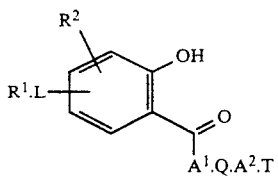

wherein T is chosen from the values defined for M, themselves obtained from compounds of formula Ic, wherein Zb is oxy, by oxidative cleavage of the unsaturated linkage bearing Ra, using techniques known in the art.

(L) For a compound of formula I wherein >X—Y—Z— has the value (c) defined above, but wherein Zb is oxy or thio, by reacting a benzofuran or a benzothiophene of the formula XV

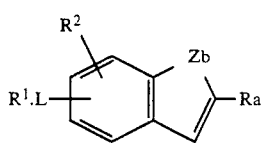

with an alkylating agent of the formula U.A¹.Q.A².M, defined above, by methods similar to those described hereinabove in process (D).

(M) For a compound of formula I wherein >X—Y—Z— has the value (a) defined above, but wherein Rb and Rc are hydrogen, catalytic hydrogenation of an indole of formula I wherein >X—Y—Z— has the value (a) defined above, but wherein Rb and Rc, together with the existing carbon to carbon bond, form an unsaturated linkage.

Particularly suitable catalytic hydrogenation conditions are those of catalytic transfer hydrogenation, for example, palladium-on-carbon (10% w/w) and formic acid (99%) a temperature in the range of, for example, 15°–100° C. and, more preferably in the range 70°–85° C.

(N) For a compound of formula I wherein >X—Y—Z— has the value (b) defined above, but wherein Za has the value —N(Rd)— and A¹ is methylene, a modified version of process (A) or (E) described above comprising cross coupling an indazole of formula XVI,

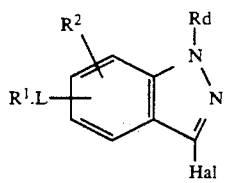

with a compound of formula Hal.CH₂.Q.A².T, but wherein T is COORh or CN, and wherein the Hal may be the same as that of XVI or different, to afford the corresponding III or VII, wherein >X—Y—Z— has the value (b) defined above, but wherein Za has the value —N(Rd)— and A¹ is methylene; followed by conversion of the COORh group or the CN group, respectively, into one of the values defined above for M by application of process (A) or (E), respectively.

The process may be carried out, for example, using a stoichiometric amount of activated zinc dust and a catalytic quantity of a transition metal catalyst, such as, for example, dichloro[1,1'-bis(diphenylphosphino)ferrocene]palladium (II) or dichlorobis(triphenylphosphine)nickel (II) to couple, for example, 3-bromo-5-(cyclopentyloxycarbonyl)amino-1-methylindazole with, for example, methyl 4-bromomethyl-3-methoxybenzoate to afford methyl 4-[5-(cyclopentyloxycarbonyl)amino-1-methylindazol-3-ylmethyl]-3-methoxybenzoate; followed by decomposition of the ester to afford 4-[5-(cyclopentyloxycarbonyl)amino-1-methylindazol-3-ylmethyl]-3-methoxybenzoic acid.

(O) For a compound of formula I wherein >X— stands for the group >N—, alkylation of an amino compound of formula XVII,

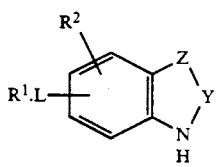

XVII with an alkylating agent of the formula U.A$^1$.Q.A$^2$.M in the presence of a suitable base, such as potassium carbonate or sodium methoxide in a solvent such as acetone, methanol or dimethylformamide.

In general, when a compound of formula I wherein M is a carboxylic acid is required, it is preferred to carry out one of the procedures (B), (C), (D), (F), (H), (I), (J), (K), (L), (M), (N) and (O) mentioned above using an appropriate carboxylic ester and liberating the required acid as a final step using procedure (A) above.

Pharmaceutically acceptable salts may be obtained using standard procedures well known in the art, for example, by reacting a compound of formula I with a suitable base affording a physiologically acceptable cation or by reacting a sufficiently basic compound of formula I with a suitable acid affording a physiologically acceptable anion.

The necessary starting materials for the above procedures may be made by procedures which are selected from standard techniques of heterocyclic chemistry, techniques which are analogous to the synthesis of known, structurally similar compounds, and techniques which are analogous to the above described procedures. Thus, for example, certain of the starting esters of formula III and certain of the starting nitriles of formula VII, respectively, may be made using general procedures similar to these described in (D), (H), (L) and (O) by using U.A$^1$.Q.A$^2$.COORh and U.A$^1$.Q.A$^2$.CN, respectively, as alkylating agents. Also, certain of the starting esters of formula III and certain of the starting nitriles of formula VII, may be made using similar general procedures to those described in (B), (C), (F), (I), (J), and (K), using corresponding intermediates IV, V, VIII, IX, XI, and XIII, but wherein T stands for COORh and CN, as appropriate, in said intermediates. The intermediates IX, wherein T stands for COORh and CN, may respectively be obtained from corresponding intermediates X, wherein T stands for COORh and CN; and the intermediates X, wherein T stands for COORh and CN, may respectively be obtained from the corresponding compounds III and VII, wherein >X—Y—Z— stands for >CRc—CRaRb—NRd— and Rb and Rc, together with the existing carbon-to-carbon bond, form an unsaturated linkage.

The intermediates XI, wherein T stands for COORh and CN, may respectively be obtained from the corresponding intermediates XII, wherein T stands for COORh and CN. The intermediates XIII, wherein T stands for COORh and CN, may respectively be obtained from the corresponding intermediates XIV, wherein T stands for COORh and CN; and the intermediates XIV, wherein T stands for COORh and CN, may respectively be obtained from corresponding intermediates III and VII, wherein >X—Y—Z— stands for >C=CRa—Zb— wherein Zb is oxy.

As an illustration, the amines of formula IV, wherein >X—Y—Z— stands for the group >C=CRa—NRd—, may be obtained, for example, by alkylating an appropriate nitroindole of formula XVIII

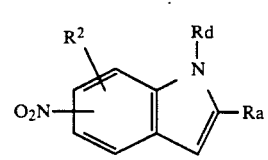

XVIII using a corresponding alkylating agent of the formula U.A$^1$.Q.A$^2$.T in the presence of a suitable Lewis acid such as silver oxide and in a solvent such as dioxane, followed by a conventional reduction, as illustrated in the accompanying examples. As an additional, similar illustration, the amines of formula IV, wherein T stands for COORh, CN, or one of the values defined for M and wherein >X—Y—Z— stands for >C=CRa—Zb— wherein Zb is S, may be obtained, for example, by alkylating an appropriate nitrobenzothiophene of structure XIX

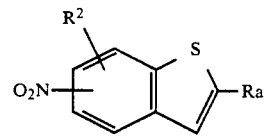

XIX using a corresponding alkylating agent of the formula U.A$^1$.Q.A$^2$.T in the presence of a suitable Lewis acid such as stannic chloride and in a solvent such as dichloromethane, followed by a conventional reduction, as illustrated in the accompanying examples. As further illustration, the amines of formula IV wherein >X— stands for the group >N— may be obtained, for example, by alkylation of an appropriate nitrobenzimidazole, nitrobenzoxazine, nitrobenzotriazole, or nitroindazole of formula XX

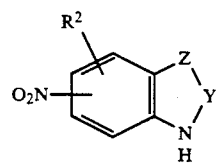

XX using a corresponding alkylating agent of the formula U.A$^1$.Q.A$^2$ T in the presence of a suitable base, such as potassium carbonate or sodium methoxide, in a solvent such as acetone or methanol, followed by a conventional reduction to give the required amine of formula IV, as illustrated in the accompanying examples.

The nitriles of formula VII may be obtained from the corresponding compounds of formula I wherein M is carboxy by treatment with, for example, chlorosulphonyl isocyanate and N,N-dimethylformamide. Alternatively, the cyano compounds of formula VII may be obtained by conventional dehydration of the primary amide of the corresponding carboxylic acid of formula I wherein M is carboxy.

It will be recognized that the starting materials of formula V for procedure (C) are also compounds of formula I wherein Rd is hydrogen, and may be obtained by any of the procedures described above for such compounds.

The starting materials of formula VI may be obtained by catalytic reduction of the appropriate nitroindole of formula XVIII, followed by acylation of the resultant aminoindole using the same general procedure as described in (B) above.

Starting materials of formula XV, but wherein Zb has the value thio, may be obtained by conventional reduction of the nitro group of the corresponding nitrobenzothiophene of formula XIX, followed by conversion of the resultant aminobenzothiophene into the said starting material XV by processes analogous to those described in process (B) or process (F).

Starting materials of formula XVI may be obtained by conventional reduction of the nitro group of appropriate nitroindazole of formula XXI,

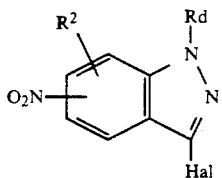

XXI followed by conversion of the resultant aminoindazole into the said starting material XVI by processes analogous to those described in process (B) and process (F).

The majority of the starting materials of formula III, IV (and its nitro precursors), VI (Rd other than hydrogen), VII, VIII, IX, X, XI, XII, XIII, XIV, XV, XVI, and XVII are novel and are provided as further features of the invention based on their utility as chemical intermediates.

As stated previously, the compounds of formula I possess leukotriene antagonist properties. Thus, they antagonise the actions of one or more of the arachidonic acid metabolites known as leukotrienes, for example, $C_4$, $D_4$, and/or $E_4$, which are known to be powerful spasmogens (particularly in the lung), to increase vascular permeability and have been implicated in the pathogenesis of asthma and inflammation (see J. L. Marx, Science, 1982, 215, 1380–1383) as well as of endotoxic shock (see J. A. Cook, et al., J. Pharmacol. Exp. Ther., 1985, 235, 470) and traumatic shock (see C. Denzlinger, et al., Science, 1985, 230, 330). The compounds of formula I are thus useful in the treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, psoriasis, as well as vasospastic cardiovascular disease, and endotoxic and traumatic shock conditions.

The compounds of formula I are potent leukotriene antagonists and are useful whenever such activity is desired. For example, the compounds of formula I are of value as pharmacological standards for the development and standardization of new disease models and assays for use in developing new therapeutic agents for treating the diseases in which the leukotrienes are implicated.

When used in the treatment of one or more of the above mentioned diseases, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; in the form of aerosols or nebuliser solutions or suspensions for administration by inhalation; and in the form of powders together with pharmaceutically acceptable inert solid diluents such as lactose for administration by insufflation.

For oral administration a tablet or capsule containing up to 250 mg. (and typically 5 to 100 mg.) of a compound of formula I may conveniently be used. Similarly, for intravenous or intramuscular injection or infusion a sterile solution or suspension containing up to 10% w/w (and typically 0.05 to 5% w/w) of a compound of formula I may conveniently be used.

The dose of compound of formula I to be administered will necessarily be varied according to principles well known in the art taking account of the route of administration and the severity of the condition and the size and age of the patient under treatment. However, in general, a compound of formula I will be administered to a warm-blooded animal (such as man) so that a dose in the range of, for example, 0.05 to 25 mg./kg. (and usually 0.5 to 10 mg./kg.) is received.

The leukotriene antagonist properties of a compound of formula I may be demonstrated using standard tests. Thus, for example, they may be demonstrated in vitro using the standard guinea-pig tracheal strip preparation described by Krell (J. Pharmacol. Exp. Ther. 1979, 211, 436). Using tis procedure, tracheal tissue strips are set up in groups of eight, four being used as time/vehicle controls and four for each test compound. All of the strips are exposed to $8 \times 10^{-9}$M leukotriene E ($LTE_4$) following the 50 minute equilibration period, and the response is recorded. This $8 \times 10^{-9}$M concentration of $LTE_4$ is that which produces a contraction equal to about 70-80% of the maximal effect of the agonist in this tissue. The $LTE_4$ is washed out for 40-45 minutes and the procedure is repeated twice to ensure that reproducible responses are being obtained with $LTE_4$. Leukotriene $C_4(LTC_4)$ or $D_4(LTD_4)$, at a concentration of $8 \times 10^{-9}$M, may be substituted for $LTE_4$ in the same procedure.

Once tissue reproducibility has been established, test compounds are added to four baths following the 40-45 minute washout period. After a 10 minute incubation with test compound or vehicle, $8 \times 10^{-9}$M $LTE_4$, $LTD_4$ or $LTC_4$ is added and the response recorded. The percentage inhibition by the test compound or the percentage change in vehicle controls is calculated, for each tissue, according to the following equation: % inhibition=100 multiplied by (mg. tension increase of preceding response minus mg. tension increase in presence of compound) divided by mg. tension increase of preceding response. The mean percentage change for vehicle controls and test compound are calculated and evaluated for significant differences by Students' t-test for unpaired data. Tissues exposed to test compounds were retested for responsiveness to $LTE_4$, $LTD_4$ or $LTC_4$ following a 25 minute washout period. If tissue responsiveness was equal to responsiveness preceding exposure to the test compound additional studies were conducted. If responsiveness was not restored by the washing procedure, the tissues were discarded. The cyclooxygenase inhibitor, indomethacin, is present at $5 \times 10^{-6} M$ in all the determinations.

In general, the compounds of formula I demonstrate statistically significant activity as $LTC_4$, $LTD_4$ and/or $LTE_4$ antagonists in the above test at a concentration of about $10^{-5} M$ or much less.

The selectivity of action as leukotriene antagonists as opposed to non-specific smooth muscle depressants may be shown by carrying out the above in vitro procedure using the non-specific spasmogen barium chloride at a concentration $1.5 \times 10^{-3} M$, again in the presence of indomethacin at $5 \times 10^{-6} M$.

Activity as a leukotriene antagonist may also be demonstrated in vivo in laboratory animals, for example, in a routine guinea-pig aerosol test in which guinea-pigs are pre-dosed with test compound (generally between 15 minutes to 1 hour) before an aerosol challenge of leukotriene $LTD_4$ (30 micrograms/ml.) and the effect of the test compound on the average time of leukotriene initiated change in breathing pattern (such as onset of dyspnoea) recorded and compared with that in un-dosed, control guinea-pigs. In general, compounds of formula I produce a significant increase in the time of onset of leukotriene initiated breathing changes following either oral or intravenous administration or by inhalation at a dose of 100 mg./kg., or much less, without any indication of untoward side-effects at several multiples of the minimum effective dose.

The invention will now be illustrated by the following non-limiting examples in which, unless stated otherwise:

(i) all operations were carried out at room or ambient temperature, that is, at a temperature in the range 18°-25° C.;

(ii) evaporation of solvent was carried out using a rotary evaporator under reduced pressure (600–4000 pascals; 4.5–30 mm. Hg) with a bath temperature of up to 60° C.;

(iii) flash chromatography was carried out on Merck Kieselgel (Art 9385) and column chromatography on Merck Kieselgel 60. (Art 7734): [these material were obtained from E. Merck, Darmstadt, W. Germany]; thin layer chromatography (TLC) was carried out on Analtech 0.25 mm. silica gel GHLF plates (Art 21521), obtainable from Analtech, Newark, Del., USA;

(iv) the course of reactions was followed by TLC and reaction times are given for illustration only:

(v) melting points are uncorrected and 'd' indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only and, for crystalline end-products, refer to the weight of recrystallized solid;

(viii) when given, NMR data is in the form of delta values for major diagnostic protons, given in parts per million (ppm) relative to tetramethylsilane (TMS) as internal standard, determined at 80 MHz or 250 MHz using $CDCl_3$, $DMSO-d_6$ or $CD_3OD$ as solvent: conventional abbreviations for signal shape are used for example, s, singlet; d, doublet; m, multiplet: br, broad; etc.; in addition "Ar" signifies an aromatic signal;

(ix) reduced pressures are given as absolute pressures in Pascals; other pressures are given as gauge pressures in bars; and (x) chemical symbols have their usual meanings; the following abbreviations. have also been used: v (volume), w (weight); m.p. (melting point), l. [liter(s)], ml. (milliliters), g. [gram(s)]; in certain Examples and Tables *, -, and # are used to indicate that an explanatory footnote applies, and in certain Tables formula 1 and formula 2 indicate those set out.

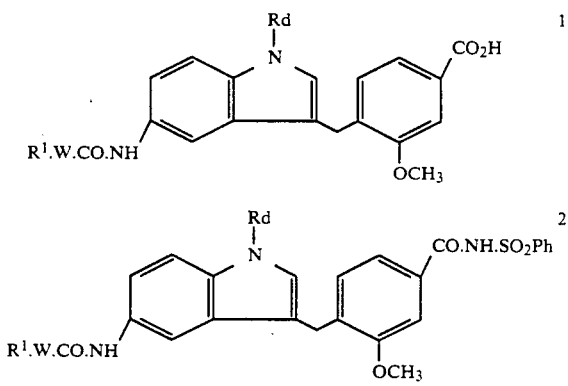

EXAMPLE 1

Methyl 4-(5-Hexanamidoindol-3-ylmethyl)-3-methoxybenzoate

A stirred solution of methyl 4-(5-aminoindol-3-ylmethyl)-3-methoxybenzoate (A) (0.2 g.) in dichloromethane (5 ml.) under an atmosphere of nitrogen, was treated with N-methylmorpholine (0.25 g.), followed by hexanoyl chloride (0.103 g.). After being stirred for 2 hours, the mixture was poured into 1M hydrochloric acid (20 ml.). This mixture was extracted with ethyl acetate (2x20 ml.). The combined organic extracts were dried (MgSO4) and evaporated. The yellow oil obtained was purified by flash chromatography on silica gel (75 ml.), eluting with 6:4 v/v ethyl acetate:hexane, to give the title compound (0.24 g., 92%) as a colorless oil: NMR: 0.83 (t,3 H, $CH_2.CH_3$), 1.36 (m,4 H, $CH_2.CH_2.CH_3$), 1.57 (quintet,2 H, $CH_2.CH_2CON$), 2.24 (t, 2 H, $CH_2.CON$), 3.80 (s,3 H, $COOCH_3$), 3.90 (s,3 H, $OCH_3$), 3.99 (s,2 H, $CH_2.Ar$), 7.1 (m, 2 H), 7.21 (m,2 H), 7.44 (m,2 H), 7.69 (s,1 H,$H^4$-indole), 9.59 (s,1 H, CONH), 10.77 (s,1 H, $H^1$-indole).

The amino ester (A) was obtained as follows:

(a) Silver (I) oxide (7.15 g.) was added to a solution of 5-nitroindole (5 g.) and methyl 4-bromomethyl-3-methoxybenzoate (B) (7.99 g.) in dioxane (30 ml.), under a nitrogen atmosphere. The mixture was stirred at 60° C. for 20 hours, dioxane removed by evaporation and ethyl acetate (50 ml.) added to the residue. The resulting suspension was separated by filtration through diatomaceous earth. The filtrate was evaporated to give a dark viscous oil, which was purified by flash chromatography on silica gel (600 ml.), eluting with 3:7 v/v ethyl acetate:hexane. The viscous yellow oil obtained was crystallized from a mixture of dichloromethane and hexane to give methyl 3-methoxy-4-(5-nitroindol-3-ylmethyl)benzoate (C) (4.6 g., 45%) as yellow needles, m.p. 153°–155° C. NMR: 3.83 (s,3 H, COOCH$_3$), 3.93 (s,3 H, OCH$_3$), 4.12 (s,2 H, CH$_2$.Ar), 7.25 (d,1 H), 7.43 (d,1 H), 7.49 (m,3 H), 7.95 (dd,1 H, H$^6$-indole), 8.47 (d,1 H, H$^4$-indole), 11.65 (broad s,1 H, H$^1$-indole).

(b) Palladium-on-carbon (10% w/w; 0.25 g.) was added to a solution of (C) (1.5 g.) in tetrahydrofuran (50 ml.) in a hydrogenation bottle. The mixture was hydrogenated at 3.45 bars for 2 hours. The catalyst was removed by filtration through diatomaceous earth and the filtrate was evaporated. The residual oil was purified by flash chromatography on silica gel (200 ml.) eluting with 1:1 v/v ethyl acetate:hexane, to give methyl 4-(5-aminoindol-3-ylmethyl)-3-methoxybenzoate (A) (1.12 g., 82%) as a viscous oil; NMR: 3.29 (br,2 H,NH$_2$), 3.88 (s,3 H, CO.OCH$_3$), 3.91 (s,3 H, OCH$_3$), 4.03 (s,2 H, CH$_2$.Ar), 6.64 (dd,1 H), 6.78 (m,2 H), 7.10 (m,2 H), 7.44 (m,2 H), 7.68 (br,1 H, H$^1$-indole).

The starting bromomethyl compound (B) was itself obtained as follows:

(c) A solution of 3-methoxy-4-methylbenzoic acid (6.0 g.) in methanol (120 ml.) was treated with acetyl chloride (6 ml.) and stirred for 36 hours. The solution was evaporated. The residue was dissolved in methanol (100 ml.) and the solution evaporated. This procedure was repeated to give methyl 3-methoxy-4-methylbenzoate (6.34 g., 98%) as a colorless oil; NMR: 2.2 (s,3 H, CH$_3$), 3.9 (2s,6 H, 2×OCH$_3$), 7.1 (d,1 H), 7.5 (m,2 H).

(d) A stirred solution of the ester from (c) (121.2 g.) in carbon tetrachloride (1.4 l.) was heated under gentle reflux with a 350 watt tungsten lamp and subjected to an air purge by means of a T-tube attached to a water aspirator. A solution of bromine (107.2 g.) in carbon tetrachloride (500 ml.) was added dropwise over 4 hours. Evaporation of the solvent gave a light yellow solid which was triturated with 500 ml. of 1:9 v/v ether:hexane. The solid was collected by filtration to give methyl 4-bromomethyl-3-methoxybenzoate (B) (111.7 g., 64%) as a pale yellow solid, m.p. 87°–90° C.; NMR: 3.9 (2s,6 H, 2×OCH$_3$), 4.5 (s,2 H, BrCH$_2$), 7.4 (m,3 H).

EXAMPLE 2

Methyl 4-[5-(2-Ethylhexanamido)indol-3-ylmethyl]-3-methoxybenzoate

Using a similar procedure to that described in Example 1, but starting from 2-ethylhexanoyl chloride and (A), there was obtained the title compound in 6% yield; partial NMR: 0.84 (m,6 H, 2×CH$_3$), 1.24 [m,6 H, (CH$_2$)$_3$], 2.24 (m,1 H, CHCON), 10.78 (d,1 H, NH).

EXAMPLE 3

Methyl 4-[5-(Cyclopentyloxycarbonyl)aminoindol-3-ylmethyl]-3-methoxybenzoate

Cyclopentyl chloroformate was added to a stirred solution of the amino ester (A) (0.15 g.) and N-methyl-morpholine (0.27 g.) in dichloromethane (3 ml.) at 0°–5° C., under an atmosphere of nitrogen. The mixture was stirred for 30 minutes at 0°–5° C., the cooling bath removed, and stirring continued for 1 hour. The mixture was then poured into 1M hydrochloric acid (15 ml.), and extracted with ethyl acetate. The combined extracts were dried (MgSO$_4$) and evaporated. The residual oil was purified by flash chromatography on silica gel (50 ml.), eluting with 3:7 v/v ethyl acetate:hexane, to give the title compound (0.18 g., 89%) as a colorless oil; NMR: 1.66 (m, 6 H), 1.82 (m,2 H), 3.83 (s,3 H, CO.OCH$_3$), 3.92 (s,3 H, OCH$_3$), 3.97 (s,2 H, CH$_2$.Ar), 5.04 (m,1 H, —CHO—), 7.09 (m, 3 H), 7.22 (d,1 H), 7.42 (dd,1 H), 7.48 (d,1 H), 7.57 (br,1 H), 9.18 (br,1 H, CONH), 10.57 (s,1 H, H$^1$-indole).

EXAMPLE 4

Methyl 4-(5-Hexanamido-1-methylindol-3-ylmethyl)-3-methoxybenzoate

Hexanoylchloride (0.029 g.) was added to a stirred solution of methyl 4-(5-amino-1-methylindol-3-ylmethyl)-3-methoxybenzoate (D) (0.05 g.) and N-methylmorpholine (0.05 g.) in dichloromethane (3 ml.), under an atmosphere of nitrogen. The mixture was stirred for 2 hours and then poured into 1M hydrochloric acid (15 ml.). This mixture was extracted with ethyl acetate (2×20 ml.). The combined extracts were dried (MgSO$_4$), and evaporated. The residual oil was purified by flash chromatography on silica gel (50 ml.), eluting with 4:6 v/v ethyl acetate:hexane, to give a colorless oil, which was crystallized from a mixture of toluene and hexane to give the title compound (0.05 g, 65%) as a white powder: NMR: 0.86 (t, 3 H, CH$_2$.CH$_3$), 1.28 (m,4 H, CH$_2$.CH$_2$.CH$_3$), 1.57 (quintet, 2 H, CH$_2$.CH$_2$.CON), 2.25 (t,2 H, CH$_2$.CH$_2$.CON), 3.69 (s,3 H, NCH$_3$), 3.82 (s,3 H, CO.OCH$_3$), 3.92 (s,3 H, OCH$_3$), 3.97 (s, 2 H, CH$_2$.Ar), 7.05 (s,1 H), 7.13 (d,1 H), 7.27 (d,1 H), 7.28 (d,1 H), 7.40 (dd,1 H), 7.48 (s,1 H), 7.74 (s,1 H), 9.61 (s,1 H).

The amino-ester (D) was prepared as follows:

(a) Methyl 3-methoxy-4-(5-nitroindol-3-ylmethyl)-benzoate (C) (0.44 g.) was added to a stirred suspension of oil-free sodium hydride (0.031 g.) in dry tetrahydrofuran (10 ml.), under an atmosphere of nitrogen. The dark-red solution was stirred for 10 minutes, and iodomethane (0.18 g.) was added. The mixture was stirred for 30 minutes, and was poured into 1M hydrochloric acid (30 ml.). The mixture obtained was extracted with ethyl acetate (2×50 ml.). The combined extracts were washed with brine (25 ml.), then dried (MgSO$_4$), and evaporated. The yellow oil obtained was purified by flash chromatography on silica gel (50 ml.), eluting with 50:45:5 v/v/v hexane:dichloromethane:ethyl acetate, to give methyl 3-methoxy-4-(1-methyl-5-nitroindol-3-ylmethyl)benzoate (E) (0.33 g., 72%) as a yellow oil, which was crystallized from dichloromethane/hexane to give a yellow solid, m.p. 144°–146° C.; NMR: 3.81 (s,3 H, N.CH$_3$), 3.83 (s,3 H, CO.OCH$_3$), 3.92 (s,3 H, OCH$_3$), 4.11 (s,2 H, CH$_2$.Ar), 7.27 (d,1 H), 7.37 (s,1 H, H$^2$-indole), 7.49 (m,2 H), 7.60 (d,1 H), 8.01 (dd,1 H, H$^6$-indole), 8.50 (d,1 H, H$^4$-indole).

(b) A solution of (E) (0.56 g.) in tetrahydrofuran (30 ml.) was hydrogenated in the presence of palladium-on-carbon (10% w/w; 0.1 g.), as described for the amino ester (A) in Example 1, to give methyl 4-(5-amino-1-methylindol-3-ylmethyl)-3-methoxybenzoate (D) (0.50 g., 98%) as pale yellow foam; NMR: 3.6 (s, 3 H, NCH$_3$), 3.8 (s,3 H, CO.OCH$_3$), 3.9 (br s,5 H, OCH$_3$ and CH$_2$.Ar), 4.45 (br,2 H, NH$_2$), 6.54 (m,2 H), 6.86 (s,1 H), 7.04 (m,2 H), 7.40 (m,2 H).

EXAMPLE 5

Methyl 4-[5-(2-Ethylhexanamido)-1-methylindol-3-ylmethyl]-3-methoxybenzoate

Using a similar procedure to that described in Example 4, but starting from 2-ethylhexanoyl chloride and (C), there was obtained the title compound in 80% yield as a viscous oil; partial NMR: 0.84 (m,6 H, 2×CH$_3$), 1.24 [m,6 H, (CH$_2$)$_3$], 2.23 (m,1 H, CH.CON), 3.70 (s,3 H, NCH$_3$).

EXAMPLE 6

Methyl 4-(1-Benzyl-5-hexanamidoindol-3-ylmethyl)-3-methoxybenzoate

Potassium t-butoxide (0.04 g.) was added to a stirred solution of methyl 4-(5-hexanamidoindol-3-ylmethyl)-3-methoxybenzoate (0.15 g.) in dry tetrahydrofuran (5 ml.), under an atmosphere of nitrogen. The resulting dark-green mixture was stirred for 30 minutes. Benzyl bromide (0.062 g.) was added, causing the color to change to light brown. After 1 hour, the mixture was poured into 1M hydrochloric acid (20 ml.). This mixture was extracted with ethyl acetate (2×25 ml.). The combined extracts were dried (MgSO$_4$) and evaporated. The brown oil obtained was purified by flash chromatography on silica gel (50 ml.), eluting with 3:7 v/v ethyl acetate:hexane, to give the title compound (0.04 g, 17%) as an oil; NMR: 0.86 (t,3 H, CH$_2$.CH$_3$), 1.27 (m,4 H, CH$_2$.CH$_2$.CH$_3$), 1.57 (m,2 H, CH$_2$.CH$_2$.CON), 2.24 (t,2 H, CH$_2$.CH $_2$.CON), 3.82 (s,3 H, CO.OCH$_3$), 3.91 (s,3 H, OCH$_3$), 3.99 (s,2 H, CH$_2$.Ar), 5.32 (s,2 H, NCH$_2$Ph), 7.21 (m,10 H), 7.44 (m,2 H), 7.75 (d, 1 H), 9.64 (s,1 H, NH).

EXAMPLE 7

Methyl 4-(1-Allyl-5-hexanamidoindol-3-ylmethyl)-3-methoxybenzoate

Using a similar procedure to that described in Example 6, but using allyl bromide in place of benzyl bromide, there was obtained the title compound in 36% yield, as a viscous oil; partial NMR: 0.86 (t, 3 H, CH$_2$.CH$_3$), 1.27 (m,4 H, CH$_2$.CH$_2$.CH$_3$), 1.57 (quintet, 2 H, CH$_2$.CH$_2$.CON), 2.24 (t,2 H, CH$_2$.CON), 4.72 (d,2 H, NCH$_2$), 5.07 (dd,2 H, CH.CH$_2$), 5.99 (m,1 H, CH.CH$_2$).

EXAMPLE 8

Methyl 4-[5-(Cyclopentyloxycarbonyl)amino-1-methylindol-3-ylmethyl]-3-methoxybenzoate Cyclopentyl chloroformate (0.11 g.) was added to a stirred solution of methyl 4-(5-amino-1-methylindol-3-ylmethyl)-3-methoxybenzoate (D) (0.25 g.) and N-methylmorpholine (0.23 g.) in dichloromethane (3 ml.), under an atmosphere of nitrogen. The mixture was stirred for 2 hours and then poured into 1M hydrochloric acid (20 ml.). This acid mixture was extracted with ethyl acetate (2×30 ml.). The combined extracts were washed with saturated brine (20 ml.), dried (MgSO$_4$), and evaporated to give a viscous oil. This was purified by flash chromatography on silica gel (50 ml.), eluting with 3:7 v/v ethyl acetate:hexane, to give the title compound as a foam (0.25 g., 74%): NMR: 1.62 [m,8 H, (CH$_2$)$_4$], 3.68 (s,3 H, NCH$_3$), 3.83 (s,3 H, CO.OCH$_3$), 3.91 (s,3 H, OCH$_3$), 3.95 (s, 2 H, CH$_2$.Ar), 5.05 (m,1 H, —CHO—), 7.11 (m,2 H), 7.26 (d, 1 H), 7.43 (m,2 H), 7.59 (br,1 H), 9.18 (br,1 H, NH).

EXAMPLE 9

4-[5-(Cyclopentyloxycarbonyl)amino-1-methylindol-3-ylmethyl-3-methoxybenzoic Acid A stirred solution of methyl 4-[5-(cyclopentyloxycarbonyl)amino-1-methylindol-3-ylmethyl]-3methoxybenzoate (0.25 g.) in methanol (5 ml.) and tetrahydrofuran (4 ml.), under an atmosphere of nitrogen, was treated with a solution of lithium hydroxide monohydrate (0.12 g.) in water (2 ml.). The mixture was stirred for 20 hours and then concentrated to remove tetrahydrofuran. The resulting aqueous solution was acidified with 1M hydrochloric acid (20 ml.). The white precipitate which formed was separated by filtration, washed with a little water, and recrystallized from a mixture of toluene and hexane to give the title compound (0.212 g., 88%) as an off-white powder; m.p. 157°–158° C.

Analysis calculated for:
C$_{24}$N$_{26}$N$_2$O$_5$: C, 68.23; H, 6.20; N, 6.63.
Found: C, 68.36; H, 6.19; N, 6.36.

EXAMPLES 10–19

Using a similar procedure to that described in Example 9, the following acids of formula 1 were obtained by hydrolysis of the corresponding methyl esters:

| Ex. | R$^1$ | W | Rd | m.p. (°C.) | yield (%) |
|---|---|---|---|---|---|
| 10 | pentyl | — | H | 205–210* | 77 |
| 11 | 1-ethylpentyl | — | H | 202–203 | 87 |
| 12 | cyclopentyl | O | H | 184–186 | 80 |
| 13 | pentyl | — | methyl | 227–228 | 66 |
| 14 | 1-ethylpentyl | — | methyl | 204–208 | 66 |
| 15 | cyclopentyl | O | methyl | 157–158 | 88 |
| 16 | pentyl | — | allyl | 203–204 | 39 |
| 17 | pentyl | — | benzyl | 210–211 | 67 |
| 18 | alpha-fluoro-benzyl | — | methyl | 188–190 | 83 |
| 19 | alpha-methoxybenzyl | — | methyl | 124–126* | 53 |

*Isolated as a partial hydrate (0.25 H$_2$O)
— Direct link to R$^1$

The starting methyl esters for Examples 18 and 19 were made by conventional acylation of methyl 4-(5-amino-1-methylindol-3-ylmethyl)-3-methoxybenzoate (D) with alpha-fluorophenylacetic acid and alpha-methoxyphenylacetic acid, respectively, in the presence of 1-[3-(dimethylamino)propyl]-3-ethylcarbodiimide hydrochloride and 4-(dimethylamino)pyridine, in dichloromethane at ambient temperature. The methyl esters were obtained as viscous oils having satisfactory NMR spectra.

EXAMPLE 20

N-[4-[5-(Cyclopentyloxycarbonyl)amino-1-methylindol-3-ylmethyl]-3-methoxybenzoyl]benzenesulphonamide N,N-Diphenylcarbamoylpyridinium hydrochloride (0.132 g.) was added to a stirred solution of 4-[5-(cyclopentyloxycarbonyl)amino-1-methylindol-3ylmethyl]-3-methoxybenzoic acid (obtained as described in Example 9) (0.15 g.) and sodium hydroxide (0.35 ml. of 1M aqueous solution) in absolute ethanol (6 ml.), under an atomsphere of nitrogen. The mixture was stirred for 15 minutes, and was then partitioned between ethyl acetate (50 ml.) and water (30 ml.). The organic layer was washed successively with 1M hydrochloric acid (20 ml.) and saturated brine (20 ml.), then dried (MgSO$_4$), and evaporated to give 4-[5-(cyclopentyloxycarbonyl)amino-1-methylindol-3-ylmethyl]-3-methoxybenzoic N,N-diphenylcarbamic anhydride, as a white foam. This foam was dissolved in N,N-dimethylformamide (DMF) (3 ml.), and added to a stirred solution of the sodium salt of benzenesulphonamide (0.19 g.) in DMF (6 ml.), under an atmosphere of nitrogen. The mixture was stirred for 1 hour and then poured into 1M hydrochloric acid (40 ml.). The acid mixture was extracted with ethyl acetate (2×30 ml.). The combined extracts were dried (MgSO$_4$) and evaporated. The yellow oil obtained was purified by the following successive procedures:

(a) flash chromatography on silica gel (50 ml.) eluting with 3:7 v/v acetonitrile:dichloromethane;

(b) crystallization from a mixture of dichloromethane and hexane:

(c) flash chromatography on silica gel (50 ml.), eluting with dichloromethane (200 ml.), then 3:1 v/v dichloromethane:ethyl acetate (200 ml.), and then 1:1 v/v dichloromethane:ethyl acetate; and (d) crystallization from a mixture of ethyl acetate and hexane to give the title compound (15.9 mg., 8%), as a white solid: m.p. 125°-130° C.

Analysis calculated for:

C$_{30}$ H$_{31}$N$_3$O$_6$S: C, 64.15; H, 5.56; N, 7.48.

Found: C, 64.18; H, 5.33: N, 7.36.

EXAMPLE 21

N-[3-Methoxy-4-[5-(2-ethylhexanamido)-1-methylindol-3-ylmethyl]benzoyl]benzenesulphonamide Using a similar procedure to that described in Example 20, the title compound was obtained in 20% yield as a solid, m.p. 169°-171° C., starting from 4-[5-(2-ethylhexanamido)-1-methylindol-3-ylmethyl]-3-methoxybenzoic acid.

EXAMPLE 22

Methyl 4-[5-(Cyclopentyloxycarbonyl)amino-1-cyclopropylmethylindol-3-ylmethyl]-3-methoxybenzoate Using a similar procedure to that described in Example 8, the title compound was obtained in 90% yield, as a viscous oil; partial NMR: 0.32 (m,2 H), 0.46 (m,2 H), 2.18 (m,1 H), 1.67 (m,6 H), 3.82 (s,3 H, OCH$_3$), 3.92 (s,3 H, OCH$_3$). The compound was made by starting from methyl 4-(5-amino-1-cyclopropylmethylindol-3-ylmethyl)-3-methoxybenzoate (itself made by analogy with (D) in Example 4, that is by reaction of the nitroindole derivative (C) with cyclopropylmethyl bromide in the presence of sodium hydride, followed by catalytic hydrogenation of the product);

EXAMPLE 23

Methyl 4-[5-(Cyclopentyloxycarbonyl)amino-1-(3-methylbut-2-enyl)indol-3-ylmethyl]-3-methoxybenzoate Using a similar procedure to that described in Example 8, the title compound was obtained in 70% yield, as a viscous oil; partial NMR: 1.64 (m,4 H), 1.69 (s,3 H, CH$_3$), 1.78 (s,3 H, CH$_3$), 3.82 (s,3 H, OCH$_3$), 3.92 (s,3 H, OCH$_3$), 4.64 (d,2 H, NCH$_2$). The compound was made by starting from methyl 4-[5-amino-1-(3-methylbut-2-enyl)indol-3-ylmethyl]-3-methoxybenzoate (F).

The amino-indole derivative (F) was obtained as follows:

A slurry of methyl 4-[1-(3-methylbut-2-enyl)-5-nitroindol-3-ylmethyl]-3-methoxybenzoate (0.22 g.) and stannous chloride dihydrate (1.6 g.) in absolute ethanol (8 ml.) was heated and stirred under reflux under an atmosphere of nitrogen for 24 hours. The cooled mixture was poured into saturated sodium bicarbonate solution (30 ml.). The mixture obtained was extracted with dichloromethane (2×30 ml.). The combined extracts were washed with saturated brine (25 ml.), dried and evaporated to give methyl 4-[5-amino-1-(3-methylbut-2-enyl)indol-3-ylmethyl]-3-methoxybenzoate (F) (0.14 g.: 69%) an oil; NMR: 1.68 (s,3 H, =C—CH$_3$), 1.76 (s,3 H, =C—CH$_3$), 3.82 (s,3 H, CO.OCH$_3$), 3.89 (s,2 H, CH$_2$.Ar), 3.91 (s,3 H, OCH$_3$), 4.57 (d,2 H, CH$_2$N), 5.27 (t,$\overline{1}$ H, CH$_2$CH), 6.48 (m,2 H), 6.91 (s,1 H), 7.04 (d,1 H), 7.08 (d,1 H), $\overline{7}$.46 (m,2 H).

EXAMPLES 24-25

Using a similar procedure to that described in Example 9, but starting from the corresponding methyl ester, the following acids of formula 1 were obtained:

Example 24: 4-[5-(cyclopentyloxycarbonyl)amino-1-cyclopropylmethylindol-3-ylmethyl]-3-methoxybenzoic acid in 72% yield, as a solid, m.p. 177°-179° C.; and Example 25: 4-[5-(cyclopentyloxycarbonyl)amino-1-(3-methylbut-2-enyl)indol-3-ylmethyl]-3-methoxybenzoic acid in 52% yield, as a solid, m.p. 179°-180° C.

EXAMPLE 26

Methyl 4-(6-hexanamido-2,3-dihydrobenz-1,4-oxazin-4-ylmethyl)-3-methoxybenzoate

Hexanoyl chloride (0.084 g.) was added to a stirred solution of methyl 4-(6.amino-2,3-dihydrobenz-1,4-oxazin-4-ylmethyl)-3-methoxybenzoate (L) (0.2 g.) in dichloromethane (20 ml.), under an atmosphere of nitrogen. The mixture was stirred for one hour and then diluted with dichloromethane (40 ml.). This mixture was washed with water, dried (MgSO$_4$) and evaporated. The residual oil was dissolved in 3:7 v/v ethyl acetate:hexane, and the solution obtained was allowed to filter through a short column of silica gel, washing with one column volume of the same solvent mixture. Evaporation of the column eluate gave the title compound (0.212 g., 82%), as a foam: NMR (250 MHz, CDCl$_3$): 0.9 (t,3 H, CH$_2$CH$_3$), 1.3 (m,4 H, CH$_3$.CH$_2$.CH$_2$), 1.6 (m,2 H, CH$_2$.$\overline{CH}_2$.CON), 2.2 (t,2 H, CH$_2$.C$\overline{ON}$), $\overline{3}$.35 (t,2 H, OC$\overline{H}_2$.CH$_2$N), 3.9 (s,6 H, OCH$_3$+CO.OCH$_3$), 4.2 (t,2 H, O$\overline{C}$H$_2$.CH$_2$N), 4.5 (s,2 H, CH$_2$—Ar), 6.8 (m,3 H), 6.9 (br s,$\overline{1}$ H, NH), 7.2 (m,1 H), $\overline{7.5}$ (m, 2 H).

The starting amino-ester (L) was itself obtained as follows:

(a) A mixture of 6-nitro-2,3-dihydrobenz-1,4-oxazine (0.45 g.), methyl 4-bromomethyl-3-methoxybenzoate (B) (0.65 g.), anhydrous potassium carbonate (0.35 g.), sodium iodide (0.38 g.) and acetone (25 ml.) was stirred and heated under reflux for 48 hours, under an atmosphere of nitrogen. The cooled reaction mixture was separated by filtration. The residue was washed with acetone, and the filtrate and washings were evaporated. The resulting solid was dissolved in dichloromethane and residual solid removed by filtration. The filtrate was evaporated. The product was purified by flash chromatography on silica gel (3 cm. diameter column), eluting with 1:10 v/v ethyl acetate: toluene, to give methyl 3-methoxy-4-(6-nitro-2,3-dihydrobenz-1,4-oxazin-4-ylmethyl)benzoate (G) (0.75 g., 84%), m.p. 130°–132° C.: NMR (80 MHz, CDCl$_3$): 3.0 (t,2 H, OCH$_2$.C$\underline{H}_2$N), 3.8 (s,3 H, OCH$_3$), 3.95 (s,3 H, OCH$_3$), 4.3 (t, 2 $\overline{H}$, OC$\underline{H}_2$.CH$_2$N), 4.5 (s,2 H, C$\underline{H}_2$.Ar), 6.8 (d,1 H), 7.5 (m, 5 H).

(b) Palladium-on-carbon (10% w/w, 0.2 g.) was added to a solution of (G) (0.69 g.) in ethyl acetate (50 ml.) in a hydrogenation bottle and the mixture hydrogenated at a pressure of 3.17 bars of hydrogen. When the uptake of hydrogen had ceased, catalyst was removed by filtration through diatomaceous earth. The filter pad was washed with ethyl acetate and the filtrate and washings were evaporated to give methyl 4-(6-amino-2,3-dihydrobenz-1,4-oxazin-4-ylmethyl)-3-methoxybenzoate (0.625 g., 91%) as a foam; NMR: 3.1 (br s,2 H, NH$_2$), 3.3 (t,2 H, OCH$_2$C$\underline{H}_2$N), 3.85 (m,6 H, OCH$_3$.+CO$_2$CH$_3$), 4.2 (t,2 H, OC$\underline{H}_2$CH$_2$N), 4.45 (s, 2 H, C$\underline{H}_2$—Ar), 6.0 (m,2 H), 6.55 (d,1 H), 7.3 (d,1 H), 7.55 (m, 2 H).

EXAMPLE 27

Methyl 4-[6-(2-Ethylhexanamido)-2,3-dihydrobenz-1,4-oxazin-4-ylmethyl]-3-methoxybenzoate Using a similar procedure to that described in Example 26 but starting from 2-ethylhexanoyl chloride, the title compound was obtained in 95% yield as a viscous oil; partial NMR: 0.89 (m,6 H, 2×CH$_3$), 1.97 (m, 1 H, CHCON), 3.91 (s,6 H, OCH$_3$+CO.OCH$_3$), 4.47 (s,2 H, C$\underline{H}_2$—Ar).

EXAMPLE 28

Methyl 4-[6-(Cyclopentyloxycarbonyl)amino-2,3-dihydrobenz-1,4-oxazin-4-ylmethyl]-3-methoxybenzoate Cyclopentyl chloroformate (0.5 g.) was added in a single portion to a stirred solution of methyl 4-(6-amino-2,3-dihydrobenz-1,4-oxazin-4-ylmethyl)-3-methoxybenzoate (L) (1.0 g.) and N-methylmorpholine (0.314 g.) in dichloromethane (30 ml.), under an atmosphere of nitrogen. After one hour, the mixture was diluted with dichloromethane and washed successively with 1M hydrochloric acid, 5% w/v sodium bicarbonate solution, and saturated brine, then dried (MgSO$_4$) and evaporated. The residue was purified by flash chromatography on silica gel (4 cm. diameter column), eluting with dichloromethane to give the title compound (0.7 g, 52%) as an oil; NMR (80 MHz, CDCl$_3$): 1.69 [m,8 H, (CH$_2$)$_4$], 3.39 (t,2 H, OCH$_2$C$\underline{H}_2$N), 3.90 (s,3 H, OCH$_3$), 3.91 (s,3 H, OCH$_3$), 4.23 (t,2 $\overline{H}$, OC$\underline{H}_2$CH$_2$N), 4.45 (s,2 H, C$\underline{H}_2$.Ar), 5.10 (m,1 H, —CHO—), 6.2 (br s,1 H, NHC$\overline{O}$), 6.59–7.62 (m,6 H).

EXAMPLE 29

4-[6-(Cyclopentyloxycarbonyl)amino-2,3-dihydrobenz-1,4-oxazin-4-ylmethyl]-3-methoxybenzoic Acid Lithium hydroxide monohydrate (0.267 g.) was added as a solid to a stirred solution of methyl 4-[6-(cyclopentyloxycarbonyl)amino-2,3-dihydrobenz-1,4-oxazin-4-ylmethyl]-3-methoxybenzoate (0.7 g.) in methanol (15 ml.) and water (2 ml.). The mixture was stirred for 12 hours then diluted with water and acidified to pH 3.35 with 3M hydrochloric acid. The precipitate which formed was isolated by filtration, washed with water and crystallized from methanol to give the title compound as a solid (0.457 g., 67%), m.p. 221°–222° C.

Analysis calculated for:

C$_{23}$H$_{26}$N$_2$O$_6$: C, 64.78; H, 6.14; N, 6.57.

Found: C, 64.77: H, 5.97; N, 6.57.

EXAMPLES 30–31

Using a similar procedure to that described in Example 29, but starting from the corresponding methyl esters, there were obtained:

Example 30: 4-[6-hexanamido-2,3-dihydrobenz-1,4-oxazin-4-ylmethyl]-3-methoxybenzoic acid in 77% yield as a solid hemi-hydrate, m.p. 207°–208° C.; and Example 31: 4-[6-(2-ethylhexanamido)-2,3-dihydrobenz-1,4-oxazin-4-ylmethyl]-3-methoxybenzoic acid in 88% as a solid, m.p. 190°–192° C.

EXAMPLE 32

N-[4-[6-(Cyclopentyloxycarbonyl)amino-2,3-dihydrobenz-1,4-oxazin-4ylmethyl]-3-methoxybenzoyl]benzenesulphonamide Benzenesulphonamide (0.037 g.) was added to a stirred solution of 4-[6-(cyclopentyloxycarbonyl)amino-2,3-dihydrobenz-1,4-oxazin-4-ylmethyl]-3-methoxybenzoic acid (0.1 g.), 1-(3-dimethylaminopropyl)-3-ethylcarbodiimide hydrochloride (0.046 g.) and 4-(dimethylamino)pyridine (0.029 g.) in dichloromethane (5 ml.), under an atmosphere of nitrogen. The mixture was stirred for 21 hours and then diluted with dichloromethane. This mixture was washed successively with 1M hydrochloric acid (2×10 ml.), 5% w/v sodium bicarbonate solution (2×10 ml.), and saturated brine (20 ml.). It was then dried (MgSO$_4$) and evaporated. The residue was purified by flash chromatography on silica gel (3 cm. diameter column) eluting with 1:1 v/v ethyl acetate:hexane. The solid obtained was recrystallized from ethyl acetate to give the title compound as a white powder (0.071 g., 54%), m.p. 186°–187° C.

Analysis Calculated for

C$_{29}$H$_{31}$N$_3$O$_7$S: C, 61.58; H, 5.52; N, 7.43.

Found: C, 61.18; H, 5.18; N, 7.00.

EXAMPLE 33

Methyl 4-(5-Hexanamidobenzo[b]thien-3-ylmethyl)-3-methoxybenzoate

Hexanoyl chloride (0.024 g.) was added to a stirred solution of methyl 4-(5-aminobenzo[b]thien-3-ylmethyl)-3-methoxybenzoate (H) (0.06 g.), and N-methylmorpholine (0.1 ml.) in dichloromethane (3 ml.). The mixture was stirred for 1 hour and then poured into water (20 ml.). The aqueous mixture was extracted with dichloromethane (2×20 ml.). The combined extracts were dried (MgSO$_4$), and evaporated. The mixture was recrystallized from a mixture of ethyl acetate and hexane to give the title compound (0.05 g., 75%) as a colorless solid: NMR (250 MHz, DMSO-d$_6$): 0.87 (t,3 H, CH$_2$CH$_3$), 1.28 (m,4, CH$_2$.CH$_2$.CH$_3$), 1.59 (quintet,2 H, CH$_2$CH$_2$CON), 2.29 (t,2 H, CH$_2$CON), 3.84 (s, 3 H, OCH$_3$), 3.91 (s,3 H, OCH$_3$), 4.11 (s,2 H, CH$_2$—Ar), 7.14 (d,1 H), 7.34 (s,1 H), 7.49 (m,3 H), 7.86 (d,1 H), 8.11 (d, 1 H), 9.95 (s,1 H).

The amino ester (H) was obtained as follows:

(a) Stannic chloride (0.41 g.) was added to a stirred solution of 5-nitrobenzo[b]thiophene (0.28 g.) and methyl 4-bromomethyl-3-methoxybenzoate (B) (0.61 g.) in dichloromethane (5 ml.). The mixture was heated under reflux for 18 hours. The cooled mixture was poured into water (10 ml.) and extracted with dichloromethane (2×20 ml.). The combined extracts were dried (MgSO$_4$) and evaporated. The oil was purified by flash chromatography on silica gel (100 ml.) eluting with 1:9 v/v ethyl acetate:hexane. The solid obtained was crystallized from hexane to give methyl 3-methoxy-4-(5-nitrobenzo[b]thien-3-ylmethyl)benzoate (I) as a solid (0.16 g., 30%): NMR: (250 MHz, CDCl$_3$): 3.92 (s, 3 H, OCH$_3$), 3.98 (s,3 H, OCH$_3$), 4.28 (s,2 H, CH$_2$—Ar), 7.15 (d,1 H), 7.22 (s,1 H), 7.56 (m,2 H), 7.93 (d,1 H), 8.19 (dd, 1 H): 8.73 (d,1 H).

(b) Stannous chloride dihydrate (0.38 g.) was added to a stirred solution of (I) (0.12 g.) in ethanol (5 ml.), under an atmosphere of nitrogen. The mixture was heated under reflux for 2 hours. The cooled mixture was basified with saturated aqueous sodium bicarbonate (15 ml.) and extracted with ethyl acetate (2×25 ml.). The extracts were dried (MgSO$_4$) and evaporated. The residual oil was purified by flash chromatography on silica gel (50 ml.), eluting with 3:7 v/v ethyl acetate:hexane to give methyl 4-(5-aminobenzo[b]thien-3-ylmethyl)-3-methoxybenzoate (H) (0.06 g., 54%) as an oil: NMR (80 MHz, DMSO-d$_6$): 3.84 (s,3 H, OCH$_3$), 3.91 (s,3 H, OCH$_3$), 4.03 (s,2 H, CH$_2$—Ar), 5.0 (br s,2 H, NH$_2$), 6.80 (m,2 H), 7.14 (m,2 H), 7.52 (m,3 H).

EXAMPLE 34

4-(5-Hexanamidobenzo[b]thien-3-ylmethyl)-3-methoxybenzoic Acid

Using a similar procedure to that described in Example 29, the title compound was obtained in 70% yield as a powder, m.p. 234°–235° C. (after recrystallization from a mixture of tetrahydrofuran, hexane and ethyl acetate).

Analysis calculated for:
C$_{23}$ H$_{25}$NSO$_4$: C, 67.13; H, 6.12; N, 3.40.
Found: C, 67.05; H, 6.20; N, 3.17.

EXAMPLE 35

Methyl 4-[6-(Cyclopentyloxycarbonyl)aminobenzimidazol-1-ylmethyl]-3-methoxybenzoate A solution of methyl 4-(6-aminobenzimidazol-1-ylmethyl)-3-methoxybenzoate (J) (0.63 g.) and 2,6lutidine (0.36 ml.) in dichloromethane (10 ml.) was treated with cyclopentyl chloroformate (0.33 g.). After stirring for 24 hours the solution was diluted with dichloromethane. The mixture was washed successively with 20% w/v sodium hydroxide, water, and brine, then dried (MgSO$_4$) and evaporated. The resultant residue was purified by flash chromatography on a 6×20 cm. silica gel column using 1:3 v/v hexane:ethyl acetate as the eluent to give the title compound (0.57 g., 93%): NMR: 1.7 [m,8 H, (CH$_2$)$_4$], 3.8 (s,3 H, OCH$_3$), 3.9 (s,3 H, OCH$_3$) 5.2 (m,1 H, CHO), 6.17–7.0 (br m,3 H), 7.5–7.8 (br m,4 H).

The starting amino ester (J) was obtained as follows:

(a) A solution of 6-nitrobenzimidazole (2.0 g.) and methyl 4-bromomethyl-3-methoxybenzoate (B) (3.5 g.) in methyl ethyl ketone (61 ml.) was treated with potassium carbonate (1.9 g.) and then heated under reflux for 24 hours. The solvent was then evaporated. The residue was extracted with ethyl acetate and inorganic material removed by filtration. The filtrate was evaporated. The resultant residue was purified by flash chromatography on a 6×30 cm. silica gel column using 1:1 v/v hexane:ethyl acetate as the eluent to give methyl 3-methoxy-4-(6-nitrobenzimidazol-1-ylmethyl)benzoate (K) (1.07 g., 26%); NMR: 3.9 (s,3 H, OCH$_3$), 4.0 (s,3 H, OCH$_3$), 5.7 (s,2 H, NCH$_2$), 7.4 (d, 1 H, Ar), 7.8 (d,1 H, H$^4$-benzimidazole), 8.1 (dd, 1 H, H$^5$-benzimidazole), 8.6 (br s,2 H$^{2,7}$-benzimidazole).

(b) A solution of (K) (0.77 g.) in anhydrous ethanol (23 ml.) was treated with stannous chloride dihydrate (2.6 g.). The mixture was stirred for 18 hours at 80° C. and then diluted with ethyl acetate. This mixture was washed successively with saturated sodium bicarbonate solution, water, and brine, then dried (MgSO$_4$) and evaporated to give methyl 4-(6-aminobenzimidazol-1-ylmethyl)-3-methoxybenzoate (J) (0.63 g., 90%): partial NMR: 3.4 (br s, 2 H, NH$_2$), 5.2 (s,2 H, NCH$_2$).

EXAMPLE 36

4-[6-(Cyclopentyloxycarbonyl)aminobenzimidazol-1-ylmethyl]-3-methoxybenzoic Acid A stirred solution of methyl 4-[6-(cyclopentyloxycarbonyl)aminobenzimidazol-1-ylmethyl]-3methoxybenzoate in 1:1 v/v tetrahydrofuran:methanol (7 ml.) was treated with water (1.4 ml.) and lithium hydroxide monohydrate (0.3 g.). Stirring was continued at ambient temperature for 4 hours. The solvent was then evaporated. The resultant residue was dissolved in water. The solution obtained was acidified with 10% v/v hydrochloric acid. The resultant precipitate was collected by filtration to give the title compound (0.43 g., 78%). An analytical sample was obtained as a white powder by recrystallization from aqueous ethanol; m.p. 241°–242° C.

Analysis calculated for:
C$_{22}$ H$_{23}$N$_3$O$_5$.0.6 H$_2$O: C, 62.87; H, 5.80; N, 10.0.
Found: C, 62.87; H, 5.55; N, 9.63.

EXAMPLE 37

Methyl 4-[6-(Butoxycarbonyl)aminobenzimidazol-1-ylmethyl]-3-methoxybenzoate

Using a similar procedure to that described in Example 35, but using butyl chloroformate and (J), the title compound was obtained as a solid in 34% yield; partial NMR: 0.9 (t,3 H, CH$_3$CH$_2$), 1.4 (m,2 H, CH$_3$CH$_2$), 1.6 (m,2 H, CH$_2$CH$_2$O), 4.1 (t,2 H, CH$_2$O).

EXAMPLE 38

Methyl 3-Methoxy-4-[6-(2-phenylbutanamido)benzimidazol-1-ylmethyl]benzoate

A solution of 1,1'-carbonyldiimidazole (0.23 g.) and 2-phenylbutyric acid (0.22 g.) in dichloromethane (3 ml.) was heated under reflux for 30 minutes and then treated with a solution of (J) (0.41 g.) in dichloromethane (3 ml.). The mixture was heated under reflux for an additional 10 minutes and then diluted with dichloromethane. This mixture was washed successively with 10% v/v hydrochloric acid, water, and brine, then dried (MgSO$_4$) and evaporated. The resultant residue was purified by flash chromatography on a 5×25 cm. silica gel column using 3:97 v/v methanol:dichloromethane as the eluent to give the title compound (0.15 g., 25%): partial NMR: 2.0 (br m,2 H, CH$_3$C$\underline{H}_2$), 3.4 (t,1 H, CH$_2$C$\underline{H}$), 7.3 (s,5 H, Ar).

EXAMPLES 39–40

Using a similar procedure to that described in Example 36 the following compounds of formula I were obtained by hydrolysis of the corresponding methyl esters:

Example 39: 4-[6-(butoxycarbonyl)aminobenzimidazol-1-ylmethyl]-3-methoxybenzoic acid in 22% yield as a hemihydrate, m.p. 184°–185° C.; and Example 40: 3-methoxy-4-[6-(2-phenylbutanamido)-benzimidazol-1-ylmethyl]benzoic acid in 31% yield as a solid, m.p. 256°–257° C. (d).

EXAMPLE 41

Methyl
4-[5-(Cyclopentyloxycarbonyl)amino-1-(2-methoxyethyl)indol-3-ylmethyl]-3-methoxybenzoate Using a similar procedure to that described in Example 8 (see also Example 22), the title compound was obtained in 78% yield, as an oil; partial NMR (250 MHz, DMSO-d$_6$): 1.4–1.9 [m,8 H, (CH$_2$)$_4$]; 3.19 (s,3 H, CH$_2$OM$\underline{e}$): 3.59 (t,2 H, C$\underline{H}_2$OMe); 3.82 (s,3 H, OMe); 3.91 (s, 3 H, OMe): 3.96 (s,2 H, ArC$\underline{H}_2$); 4.22 (t,2 H, C$\underline{H}_2$N); 5.08 (m, 1 H, —CHO—); 9.20 (br s,1 H, NH). The compound was made by starting from methyl 4-[5-amino-1-(2-methoxyethyl)indol-3-ylmethyl]-3-methoxybenzoate (itself made by analogy with (D) in Example 4, that is by reaction of the nitroindole derivative (C) with 1-bromo-2-methoxyethane in N,N-dimethylformamide in the presence of sodium hydride, followed by catalytic hydrogenation of the product).

EXAMPLE 42

Methyl
4-[1-(N-Ethylcarbamoylmethyl)-5-(cyclopentyloxycarbonyl)aminoindol-3-ylmethyl]-3-methoxybenzoate Using a similar procedure to that described in Example 8 (see also Example 22), the title compound was obtained in 73% yield, as a white powder; m.p. 192°–194° C.; partial NMR (250 MHz, DMSO-d$_6$) 1.01 (t,J=7.15 Hz,3 H, CH$_2$CH$_3$; 1.5–1.9 [m,8 H, (CH$_2$)$_4$]; 3.10 (m,2 H, NHC$\underline{H}_2$): 3.83 (s,3 H, OMe); 3.92 (s,3 H, OMe); 3.97 (s,2 H, ArC$\underline{H}_2$): 4.67 (s,2 H, —NCH$_2$); 5.10 (m,1 H, —CHO—); 9.25 (br s,1 H, ArN$\underline{H}$). The compound was made by starting from methyl 4-[1-(N-ethylcarbamoylmethyl)-5-aminoindol-3-ylmethyl-3-methoxybenzoate (itself made by analogy with (D) in Example 4, that is by reaction of the nitroindole derivative (C) with 2-chloro-N-ethylacetamide in N,N-dimethylformamide in the presence of sodium hydride, followed by catalytic hydrogenation of the product).

EXAMPLE 43

Methyl
4-[1-Cyclopentyl-5-(cyclopentyloxycarbonyl)aminoindol-3-ylmethyl]-3-methoxybenzoate Using a similar procedure to that described in Example 8 (see also Example 22), the title compound was obtained in 75% yield, as a foam: partial NMR (250 MHz, DMSO-d$_6$): 1.4–2.15 [m,16 H, 2×(CH$_2$)$_4$]; 3.82 (s,3 H, OMe): 3.92 (s,3 H, OMe); 3.96 (s,2 H, ArC$\underline{H}_2$); 4.80 (m,1 H, —NC$\underline{H}$): 5.10 (m,1 H, —CHO—): 9.20 (br s,1 H, NH). The compound was made by starting from methyl 4-[5-amino-1-cyclopentylindol-3-ylmethyl]-3-methoxybenzoate (itself made by analogy with (D) in Example 4, that is by reaction of the nitroindole derivative (C) with bromocyclopentane in N,N-dimethylformamide at 50° C. in the presence of sodium hydride, followed by catalytic hydrogenation of the product).

EXAMPLE 44

Methyl
4-[5-(Cyclopentyloxycarbonyl)amino-1-propylindol-3-ylmethyl]-3-methoxybenzoate Using a similar procedure to that described in Example 8 (see also Example 22), the title compound was obtained in 86% yield, as a foam; partial NMR (250 MHz, DMSO-d$_6$): 0.80 (t,J=7.30 Hz,3 H, CH$_2$CH$_3$); 1.4–1.9 [m, 10 H, (CH$_2$)$_4$ and C$\underline{H}_2$CH$_3$]; 3.83 (s,3 H, OMe); 3.92 (s,3 H, OMe); 3.96 (s,2 H, ArC$\underline{H}_2$); 4.02 (t,J=7.30 Hz,2 H, NCH$_2$): 5.05 (m,1 H, —CHO—): 9.25 (br s,1 H, NH). The compound was made by starting from methyl 4-[5-amino-1-propylindol-3-ylmethyl]-3-methoxybenzoate (itself made by analogy with (D) in Example 4, that is by reaction of the nitroindole derivative (C) with allyl bromide in N,N-dimethylformamide in the presence of sodium hydride, followed by catalytic hydrogenation of the product resulting in reduction of both nitro and allyl substituents).

EXAMPLE 45

Methyl
4-[5-(Cyclopentyloxycarbonyl)amino-1-(3-methylbutyl)indol-3-ylmethyl]-3-methoxybenzoate Using a similar procedure to that described in Example 8 (see also Example 22), the title compound was obtained in 71% yield, as a white solid: partial NMR (250 MHz, DMSO-d$_6$): 0.90 (d,J=6.38 Hz,6 H, 2×CH$_3$); 1.35–2.0 [m,11 H, (CH$_2$)$_4$ and NCH$_2$C$\underline{H}_2$C$\underline{H}$; 3.82 (s,3 H, OMe); 3.91 (s,3 H, OMe); 3.96 (s,2 H, ArC$\underline{H}_2$); 4.08 (t,2 H, NCH$_2$); 5.10 (m,1 H, —CHO—); 9.20 (br s,1 H, NH). The compound was made by starting from methyl 4-[5-amino-1-(3-methylbutyl)indol-3-ylmethyl-3-methoxybenzoate (itself made by analogy with (D) in Example 4, that is by reaction of the nitroindole derivative (C) with 4-bromo-2-methyl-but-2-ene in N,N-dimethylformamide in the presence of sodium hydride, followed by catalytic hydrogenation of the product resulting in reduction of both nitro and 2-methylbut-2-enyl substituents).

EXAMPLE 46

Methyl
4-[5-(Cyclopentyloxycarbonyl)amino-1-hexylindol-3-ylmethyl]-3-methoxybenzoate Using a similar procedure to that described in Example 6, except using sodium hydride as base, and a mixture of N,N-dimethylformamide and N,N'-dimethylpropyleneurea (80:20 v/v) as solvent, the title compound was obtained in 44% yield, as an oil: partial NMR (250 MHz, DMSO-$d_6$): 0.81 (t,J=6.70 Hz,3 H, $CH_2CH_3$); 1.21 (m,6 H): 1.4–2.0 (m,10 H): 3.83 (s,3 H, OMe): 3.92 (s, 3 H, OMe): 3.96 (s,2 H, Ar$CH_2$): 4.05 (t,J=6.85 Hz,2 H, N$CH_2$): 5.04 (m,1 H, —CHŌ—): 9.20 (br s,1 H, NH): starting from methyl 4-[5-(cyclopentyloxycarbonyl)aminoindol-3-ylmethyl]-3-methoxybenzoate.

EXAMPLE 47

Methyl 4-[5-(2-Cyclopentylacetamido)-1-methylindol-3-ylmethyl]-3-methoxybenzoate A mixture of methyl 4-(5-amino-1-methylindol-3-ylmethyl)-3-methoxybenzoate (D) (0.57 g.), cyclopentylacetic acid (0.23 g.), 4-(dimethylamino)pyridine (0.22 g.), and 1-(3-dimethylaminopropyl)-3-ethylcarbodiimide hydrochloride (0.343 g.), was dissolved in dichloromethane (25 ml.), under an atmosphere of nitrogen, and stirred at room temperature for 18 hours. The mixture was poured into 1M hydrochloric acid (25 ml.), the separated aqueous layer extracted with dichloromethane (3×25 ml.), the combined organic extracts washed with water, brine, dried (MgSO$_4$) and evaporated. The residual oil was crystallized from ethyl acetate to give the title compound (0.555 g. 73%) as a white powder; m.p. 180°–181° C.; partial NMR (250 MHz, DMSO-$d_6$): 1.17 (m,2 H); 1.4–1.8 (m,6 H); 2.25 (m,3 H); 3.70 (s,3 H, NMe); 3.82 (s,3 H, OMe); 3.92 (s,3 H, OMe); 3.97 (s,2 H, Ar$CH_2$); 9.62 (br s,1 H, NH).

EXAMPLE 48A

Methyl 4-[5-(2-Cyclopentylacetamido)-1-propylindol-3-ylmethyl]-3-methoxybenzoate Using a similar procedure to that described in Example 47, the title compound was obtained in 76% yield, as a foam; partial NMR (250 MHz, DMSO-$d_6$): 0.81 (t,J=7.30 Hz,3 H, $CH_2CH_3$; 1.15 (m,2 H); 1.4–1.7 (m, 8 H); 2.24 (m,3 H); 3.82 (s,3 H, OMe); 3.92 (s,3 H, OMe); 3.97 (s,2 H, Ar$CH_2$); 4.04 (t,2 H, N$CH_2$): 9.61 (br s,1 H, NH). The compound was made by starting from methyl 4-[5-amino-1-propylindol-3-ylmethyl]-3-methoxybenzoate.

EXAMPLE 48B–56

Using a similar procedure to that described in Example 9, there were obtained the following acids of formula 1 in which W is oxy for Examples 48B–54 and a direct link to $R^1$ for Examples 55, 56:

| Ex. | $R^1$ | Rd | m.p. (°C.) | yield (%) |
|---|---|---|---|---|
| 48B | cyclopentyl | propyl | 157–158 | 89 |
| 49 | cyclopentyl | allyl | 171–172 | 88 |
| 50 | cyclopentyl | hexyl | 152–153 | 75 |
| 51 | cyclopentyl | 2-methoxyethyl | 158–159 | 65 |
| 52 | cyclopentyl | N-ethylcarbamoylmethyl | 228–231 | 73 |
| 53 | cyclopentyl | 3-methylbutyl | 160–161 | 75 |
| 54 | cyclopentyl | cyclopentyl | 189–191 | 75 |
| 55 | cyclopentylmethyl | methyl | 238–241 | 84 |
| 56 | cyclopentylmethyl | propyl | 196–197 | 82 |

EXAMPLE 57

N-[4-[5-(Cyclopentyloxycarbonyl)amino-1-methylindol-3-ylmethyl]-3-methoxybenzoyl]benzenesulphonamide A mixture of [5-(cyclopentyloxycarbonyl)amino-1-methylindol-3-ylmethyl]-3-methoxybenzoic acid (6.0 g.), benzenesulphonamide (2.34 g.), 4-(dimethylamino)pyridine (1.84 g.), and 1-(3-dimethylaminopropyl)-3-ethylcarbodiimide hydrochloride (2.86 g.) was dissolved in dichloromethane (250 ml.), under an atmosphere of nitrogen, and the mixture stirred at room temperature for 18 hours. The mixture was poured into 1M hydrochloric acid (100 ml.), the separated aqueous layer extracted with dichloromethane (2×100 ml.), the combined organic extracts washed with water, and brine, dried (MgSO$_4$) and evaporated. The residual oil was purified by flash chromatography on silica gel (700 ml.), eluting with 45:50:5 v/v/v hexane:dichloromethane:ethyl acetate, to give a product which was precipitated from hot methanol by water, to give the title compound (7.82 g., 98%) as a white powder; m.p. 125°–130° C. (m.p. 220°–223° C., after recrystallization from methanol).

Analysis calculated for:
$C_{30}H_{31}N_3O_6S$: C, 64.15; H, 5.56; N, 7.48.
Found: C, 64.24; H, 5.66; N, 7.54.

EXAMPLES 58–66

Using a similar procedure to that described in Example 57, the following sulphonamides of formula 2 were obtained in which W is oxy for Examples 58–65 and a direct link to $R^1$ for Example 66:

| Ex. | $R^1$ | Rd | m.p. (°C.) | yield (%) |
|---|---|---|---|---|
| 58 | cyclopentyl | propyl | 109–115 | 84 |
| 59 | cyclopentyl | allyl | 116–119 | 76 |
| 60 | cyclopentyl | hexyl | 97–100 | 58 |
| 61 | cyclopentyl | hydrogen | 244–245 | 30 |
| 62 | cyclopentyl | 3-methylbutyl | 125–135 | 83 |
| 63 | cyclopentyl | 2-methoxyethyl | 107–117 | 65 |
| 64* | cyclopentyl | N-ethylcarbamoylmethyl | 132–140 | 60 |
| 65 | cyclopentyl | cyclopentyl | 179–181 | 89 |
| 66 | cyclopentylmethyl | methyl | 132–137 | 86 |

*Example 64:
Analysis calculated for: $C_{33}H_{36}N_4O_7S$: C, 62.64; H, 5.73; N, 8.85 Found: C, 62.22; H, 5.77; N, 8.78

EXAMPLE 67

Methyl 4-[6-(2-Cyclopentylacetamido)-2,3-dihydrobenz-1,4-oxazin-4-ylmethyl]-3-methoxybenzoate Using a similar procedure to that described in Example 47, but starting from benzoxazine amine (L) (and avoiding the use of excess hydrochloric acid during the work-up), the title compound was obtained 80% yield, as a white powder; m.p. 152°-153° C.; partial NMR (250 MHz, DMSO-d$_6$): 1.10-1.68 [m,8 H, (CH$_2$)$_4$]; 2.14 (m,3 H, —CHCH$_2$); 3.41 (t,2 H, NCH$_2$CH$_2$; 3.84 (s,3 H, OMe); 3.92 (s,3 H, OMe); 4.18 (t,2 H, OCH$_2$); 4.41 (s,2 H, ArCH$_2$), 9.40 (br s,1 H, NH).

EXAMPLE 68

4-[6-(2-Cyclopentylacetamido)-2,3-dihydrobenz-1,4-oxazin-4-ylmethyl]-3-methoxybenzoic Acid Using a similar procedure to that described in Example 29, the title compound was obtained in 97% yield as a yellow powder; m.p. 224°-225° C.

EXAMPLE 69

N-[4-[6-(2-Cyclopentylacetamido)-2,3-dihydrobenz-1,4-oxazin-4-ylmethyl]-3-methoxybenzoyl]benzenesulphonamide Using a similar procedure to that described in Example 32, the title compound was obtained in 61% yield as a white powder; m.p. 190°-192° C.

EXAMPLE 70

Methyl 4-[5-(Cyclopentyloxycarbonyl)aminobenzo[b]-thien-3-ylmethyl]-3-methoxybenzoate Starting from amine (H), and using a similar procedure to that described in Example 8, the title compound was obtained in 78% yield, as a white powder; m.p. 163°-164° C., partial NMR (250 MHz, DMSO-d$_6$): 1.57-1.87 [m,8 H, (CH$_2$)$_4$]; 3.84 (s,3 H, OMe); 3.92 (s,3 H, OMe); 4.11 (s,2 H, ArCH$_2$): 5.07 (m,1 H, —CHO—); 9.61 (br s,1 H, NH).

EXAMPLE 71

4-[5-(Cyclopentyloxycarbonyl)aminobenzo[b]thien-3-ylmethyl]-3-methoxybenzoic Acid Using a procedure similar to that described in Example 9, the title compound was obtained in 95% yield, as a white powder: m.p. 259°-261° C.

EXAMPLE 72

N-[4-[5-(Cyclopentyloxycarbonyl)aminobenzo[b]thien-3-ylmethyl]-3-methoxybenzoyl]benzenesulphonamide Using a similar procedure to that described in Example 57, the title compound was obtained in 51% yield, as a white powder; m.p. 253°-254° C.

EXAMPLE 73

Methyl 4-[6-(2-Cyclopentylacetamido)benzimidazol-1-ylmethyl]-3-methoxybenzoate

Starting from amine (J), and using a similar procedure to that described in Example 47, the title compound was obtained in 84% yield, as a pink powder: partial NMR (80 MHz, DMSO-d$_6$): 1.57 [br m,8 H, (CH$_2$)$_4$]; 2.26 (br s,3 H, —CHCH$_2$); 3.83 (s,3 H, OMe); 3.94 (s,3 H, OMe); 5.42 (s,2 H, NCH$_2$); 9.81 (s,1 H, NH).

EXAMPLE 74

4-[6-(2-Cyclopentylacetamido)benzimidazol-1-ylmethyl]-3-methoxybenzoic Acid

Using a similar procedure to that described in Example 9, the title compound was obtained in 62% yield, as white crystalline needles; m.p. 280°-281° C. (d).

EXAMPLES 75-76

Using a similar procedure to that described in Example 57, the following sulphonamides were obtained:

Example 75: N-[4-[6-(cyclopentyloxycarbonyl)aminobenzimidazol-1-ylmethyl]-3-methoxybenzoyl]-benzenesulphonamide in 7% yield, as a white powder; m.p. 242°-243° C.; and Example 76: N-[4-[6-(2-cyclopentylacetamido)benzimidazol-1-ylmethyl]-3-methoxybenzoyl]benzenesulphonamide in 61% yield, as a white powder; m.p. 220°-222° C. (monohydrate).

EXAMPLE 77

Methyl 4-[6-(Cyclopentyloxycarbonyl)aminobenzotriazol-1yl-methyl]-3-methoxybenzoate Using methyl 4-(6-aminobenzotriazol-1-ylmethyl)-3-methoxybenzoate (M), and a similar procedure to that described in Example 3 (see also Example 35), the title compound was obtained in 40% yield, as a solid m.p. 142°-143° C.

The starting amino ester (M) was obtained from methyl 3-methoxy-4-(6-nitrobenzotriazol-1-ylmethyl)-benzoate (N) by a similar procedure to that described in Example 1(b).

The methyl 3-methoxy-4-(6-nitrobenzotriazol-1-ylmethyl)benzoate was itself prepared from 5-nitrobenzotriazole using a procedure similar to that described in Example 35(a), in 26% yield, as a white solid; m.p. 165°-166.5° C.

EXAMPLE 78

4-[6-(Cyclopentyloxycarbonyl)aminobenzotriazol-1-ylmethyl]-3-methoxybenzoic Acid Using a similar procedure to that described in Example 9, the title compound was obtained in 24% yield, as a pink solid; m.p. 237°-239° C. (partial hydrate).

EXAMPLE 79

Methyl 4-[1-(2-Carbethoxyethyl)-5-(cyclopentyloxycarbonyl)aminoindol-3-ylmethyl]-3-methoxybenzoate Using a procedure similar to that of Example 1 (see also Example 22), the title compound was obtained in 85% yield, as a foam. Partial NMR (250 MHz, DMSO-d$_6$): 1.07 (t,3 H, —OCH$_2$CH$_3$); 1.7 [m,8 H, (CH$_2$)$_4$]; 2.76 (t,2 H, —CH$_2$CO$_2$Et); 3.82 (s,3 H, OCH$_3$); 3.91 (s,3 H, OCH$_3$); 3.93 (s,2 H, ArCH$_2$Ar); 3.94 (q,2 H, —OCH$_2$CH$_3$); 4.32 (t,2 H, —CH$_2$N); 5.10 (m,1 H, —OCH—). The compound was made by starting from methyl 4-[5-amino-1-(2-carbethoxyethyl)indol-3-ylmethyl]-3-methoxybenzoate (itself made by analogy with (D) in Example 4, that is by reaction of the nitro-indole derivative (C) with ethyl acrylate in N,N-dimethylformamide in the presence of sodium hydride, followed by catalytic hydrogenation of the product).

EXAMPLE 80

Methyl 4-[5-(2-Cyclopentylacetamido)-1-ethylindol-3-ylmethyl]-3-methoxybenzoate

Using a similar procedure to that described in Example 47, the title compound was obtained in 90% yield, as a solid: m.p. 144°-146° C.: partial NMR (250 MHz, DMSO-d$_6$): 1.18 (m,2 H, cyclopentyl ring): 1.31 (t, 3 H, —CH$_2$CH$_3$): 1.59 (m,6 H, cyclopentyl ring): 2.24 (m, 3 H): 3.82 (s,3 H, OCH$_3$): 3.92 (s,3 H, OCH$_3$): 3.97 (s,2 H, ArCH$_2$Ar): 4.09 (q,2 H, —CH$_2$CH$_3$). The compound was made by starting from methyl 4-(5-amino-1-ethylindol-3-ylmethyl)-3-methoxybenzoate (itself prepared by analogy with (D) in Example 4, except using iodoethane in place of iodomethane).

EXAMPLES 81-82

Using a similar procedure to that described in Example 9, there were obtained the following acids of formula 1:

| Ex. | R$^1$ | W | Rd | m.p. (°C.) | yield (%) |
|---|---|---|---|---|---|
| 81 | cyclopentyl | O | 2-carboxyethyl | 109-119 | 84 |
| 82 | cyclopentylmethyl | — | ethyl | 219-220 | 83 |

— Direct link to R$^1$

EXAMPLE 83

(±)Methyl 4-[5-(2-Cyclopentylacetamido)-1-ethyl-2,3-dihydroindol-3-ylmethyl]-3-methoxybenzoate Palladium-on-carbon (10% w/w, 0.5 g.) was added to a mixture of methyl 4-[5-(2-cyclopentylacetamido)-1-ethylindol-3-ylmethyl]-3-methoxybenzoate (0.5 g., prepared as described in Example 80), and formic acid (99%, 20 ml.), under an atmosphere of nitrogen. The mixture was vigorously stirred and heated at 80° C. for one hour. The cooled mixture was filtered through a pad of diatomaceous earth, the filter cake washed with methanol, and the filtrate evaporated. The resulting oil was dissolved in ethyl acetate (30 ml.) washed with water, brine, then dried (MgSO$_4$) and evaporated. The product was purified by flash chromatography on silica gel (4 cm. diameter column), eluting with 2:3 v/v ethyl acetate:hexane, to give the title compound (0.37 g., 80%) as a foam; NMR (250 MHz, DMSO-d$_6$): 1.04 (t,3 H, —CH$_2$C/e,uns/H/ $_3$); 1.15 (m,2 H, cyclopentyl ring); 1.4-1.8 (m,6 H, cyclopentyl ring); 2.2 (m,3 H); 2.7 (dd,1 H); 2.85-3.25 (m,5 H); 3.45 (m,1 H); 3.86 (s,3 H, OCH$_3$); 3.87 (s,3 H, OCH$_3$); 6.43 (d,1 H); 7.20 (m,2 H); 7.30 (d,1 H); 7.50 (m,2 H); 9.47 (s,1 H, NH).

EXAMPLE 84

(±)-4-[5-(2-Cyclopentylacetamido)-1-ethyl-2,3-dihydroindol-3-ylmethyl]-3-methoxybenzoic Acid Using a similar procedure to that described in Example 29 (see also Example 9), except using the ester described in Example 83, the title compound was obtained in 84% yield, m.p. 183°-186° C., as a partial hydrate.

EXAMPLE 85

N-[4-[6-(2-Cyclopentylacetamido)-2,3-dihydrobenz-1,4-oxazin-4-ylmethyl]-3-methoxybenzoyl]-2-methylbenzenesulphonamide Using a similar procedure to that described in Example 32 (see also Example 69), except using o-toluenesulphonamide, the title compound was obtained in 45% yield, m.p. 207°-208° C., (monohydrate).

EXAMPLE 86

Methyl 4-[5-(cyclopentyloxycarbonyl)amino-1-methylindazol-3-ylmethyl]-3-methoxybenzoate Methyl 4-[2-(acetoxyimino)-2-[5-(cyclopentyloxycarbonyl)amino-2-(methylamino)phenyl]ethyl]-3-methoxybenzoate (O) (1.3 g.) was placed in a 100 ml. round-bottomed flask charged with a stirring bar, and the flask was maintained under high vacuum by means of a vacuum pump. The flask was immersed in a preheated (170° C.) oil bath until the solid melted and for 10 minutes thereafter. The cooled product was purified by flash chromatography on silica gel (5 cm. diameter column, compound applied to column by dissolution in a small volumn of dichloromethane), eluting with 2:3 v/v ethyl acetate:hexane, to give the title compound (1.1 g., 96%) as a foam; NMR (250 MHz, DMSO-d$_6$) 1.5-1.9 [m,8 H, (CH$_2$)$_4$]; 3.83 (s,3 H, CH$_3$): 3.92 (s,3 H, CH$_3$); 3.93 (s,3 H, CH$_3$); 4.19 (s,2 H, ArCH$_2$Ar); 5.07 (m,1 H, —OCH—); 7.14 (d,1 H); 7.35 (d,1 H); 7.45-7.49 (m,3 H); 7.78 (br s, 1 H): 9.46 (br s,1 H, NH).

The oxime-acetate ester (O) was obtained as follows, starting from methyl 4-[5-(cyclopentyloxycarbonyl)amino-1-methylindol-3-ylmethyl]-3-methoxybenzoate (P), itself prepared as described in Example 8:

(a) Rose Bengal (0.025 g.) was added to a solution of methyl 4-[5-(cyclopentyloxycarbonyl)amino-1-methylindol-3-ylmethyl]-3-methoxybenzoate (P) (2.0 g.) in dry methanol (200 ml.). The resulting red solution was introduced, together with a magnetic stirring bar, into a quartz photolysis apparatus fitted with a gas bubbler, drying-tube, and a water-cooled immersion tube housing a quartz tungsten-halogen lamp (type DVY, 650 watts). Purified, dry oxygen gas was bubbled through the stirred solution while irradiating the solution. After 1.5 hours (TLC monitoring), the methanol solution was removed from the apparatus, evaporated, and filtered through a column of silica gel (6 cm. diameter column) eluting with 3:2 to 100:0 v/v ethyl acetate:hexane, to give methyl 4-2-[5-(cyclopentyloxycarbonyl)amino-2-(formyl)(methyl)aminophenyl]-2-oxoethyl]-3-methoxybenzoate (Q) (2.12 g., 98.5%) as a foam; NMR (250 MHz, DMSO-d$_6$): 1.5-1.91 [m,8 H, (CH$_2$)$_4$]; 3.04 (s,2.25 H, N-Me, isomer A); 3.24 (s,0.75 H, N-Me, isomer B); 3.79, 3.82, 3.86 (singlets,6 H, 2×OMe); 4.12 (s,0.5 H, ArCH$_2$CO, isomer B); 4.17 (s,1.5 H, ArCH$_2$CO, isomer A); 5.11 (m,1 H, —OCH—); 7.27-8.15 (2m,7 H): 9.85 (br s,0.25 H, NH, isomer B); 9.91 (br s,0.75 H, NH, isomer A).

(b) A solution of the keto-formanilide (Q) (1.0 g., prepared as described in (a) above), and hydroxylamine hydrochloride (0.84 g.) in freshly-distilled pyridine (100 ml.) was heated and stirred under reflux for 18 hours, under a nitrogen atmosphere. The cooled solution was concentrated, the residue dissolved in ethyl acetate (100 ml.), washed with water (3×25 ml.), dried (MgSO$_4$) and evaporated. The product was purified by flash chromatography on silica gel (4 cm. diameter column), eluting with 1:1 v/v ethyl acetate:hexane to give methyl 4-[2-[5-(cyclopentyloxycarbonyl)amino-2-methylaminophenyl]-2-(hydroxyimino)ethyl]-3-methoxybenzoate (R) (0.57 g., 59%) as an off-white solid; NMR (DMSO-d$_6$) : 1.4-1.9 [m,8 H, (CH$_2$)$_4$]; 2.81 (distorted doublet,3 H, NMe); 3.83 (s,3 H, OMe): 3.92 (s,3 H, OMe): 4.04 (s,2 H, ArCH$_2$CO); 4.98 (m,1 H, —CHO—); 6.57 (d,1 H): 6.93 (d,1 H); 7.24 (br m,2 H); 7.46 (m, 4 H); 8.92 (br s,1 H, NHCO).

(c) Acetic anhydride (0.27 ml., 0.29 g.) was added to a solution of the amino-oxime (R) (1.3 g., prepared as described in (b) above) and 4-(dimethylamino)pyridine (0.35 g.) in dichloromethane (120 ml.), under a nitrogen atmosphere. After 18 hours, the mixture was evaporated, the yellow residue dissolved in ethyl acetate (50 ml.), washed with hydrochloric acid (0.05N, 15 ml.), water (15 ml.), brine, dried (MgSO$_4$) and evaporated. Crystallization from ethyl acetate/hexane at −20° C. gave methyl 4-[2-(acetoxyimino)-2-[5-(cyclopentyloxycarbonyl)amino-2-methylaminophenyl]ethyl]-3-methoxybenzoate (O) (1.36 g., 96%), as a powder, m.p. 124°–126° C.; NMR (250 MHz, DMSO-d$_6$) 1.5–1.9 [m,8 H, (CH$_2$)$_4$]; 2.12 (s,3 H, OCOMe); 2.83 (distorted doublet,3 H ; NMe); 3.83 (s,3 H, OMe); 3.88 (s,3 H, OMe); 4.17 (s,2 H, ArCH$_2$C=N); 5.00 (m,1 H, —OCH—); 6.24 (d, 1 H); 7.01 (d̄,1 H); 7.3–7.5 (m,5 H); 9.1 (br s,1 H, NHCO).

EXAMPLE 87

4-[5-(Cyclopentyloxycarbonyl)amino-1-methylindazol-3ylmethyl]-3-methoxybenzoic Acid Using a similar procedure to that described in Example 9, except starting from methyl 4-[5-(cyclopentyloxycarbonyl)amino-1-methylindazol-3-ylmethyl]-3-methoxybenzoate, the title compound was obtained in 95% yield, as a white solid, m.p. 216°–217° C.

EXAMPLE 88

N-[4-[5-(Cyclopentyloxycarbonyl)amino-1-methylindazol-3-ylmethyl]-3-methoxybenzoyl]benzenesulphonamide Using a similar procedure to that described in Example 57, except starting from the acid described in Example 87, the title compound was obtained in 63% yield, as a white powder, m.p. 145° C. (hemi-hydrate).

Analysis calculated for:
C$_{29}$H$_{30}$N$_4$O$_6$S.0.5H$_2$O: C, 60.93; H, 5.46; N, 9.80.
Found: C, 60.83; H, 5.30: N, 9.79.

EXAMPLE 89

Sodium N-[4-[5-(Cyclopentyloxycarbonyl)amino-1-methylindol-3-ylmethyl]-3-methoxybenzoyl]benzenesulphonamide Sodium hydroxide solution (1 N, 10.69 ml.) was added to a stirred solution of N-4-[5-(cyclopentyloxycarbonyl)amino-1-methylindol-3-ylmethyl]-3-methoxybenzoyl]benzenesulphonamide (6.0 g.) in 1:1 v/v tetrahydrofuran:methanol (100 ml.), under a nitrogen atmosphere. After 0.5 hours, the organic solvents were removed in vacuo and the resulting aqueous solution lyophilised to give the title compound (6.1 g., 95%) as a white powder, m.p. 168°–175° C. (monohydrate).

Analysis calculated for:
C$_{30}$H$_{30}$N$_3$O$_6$SNa.H$_2$O: C, 59.89; H, 5.36; N, 6.98.
Found: C, 59.74; H, 5.24; N, 6.90.

EXAMPLE 90

Methyl 4-[6-(Cyclopentyloxycarbonyl)amino-3-methoxyindazol-1-ylmethyl]-3-methoxybenzoate Cyclopentyl chloroformate (0.17 ml.) was added to a cooled (−20° C.) solution of methyl 4-[6-amino-3-methoxyindazol-1-ylmethyl]-3-methoxybenzoate (S) (0.381 g.) and pyridine (0.11 ml.) in dichloromethane (3.0 ml.). After warming to ambient temperature, the mixture was diluted with ethyl acetate, and washed with hydrochloric acid (1N), water, brine, dried (MgSO$_4$) and evaporated. The residue was purified by flash chromatography on silica gel (56 g.), eluting with 5:95 v/v ethyl acetate:dichloromethane, to give the title compound (0.365 g., 75%) as an oil, with satisfactory NMR spectral data.

The amino-ester (S) was obtained as follows:

(a) 6-Nitroindazolol (0.206 g.) was added to a solution of sodium (0.026 g.) in methanol (1.5 ml.), and the mixture heated at 50° C. for 10 minutes. A solution of methyl 4-bromomethyl-3-methoxybenzoate (B) (0.327 g.) in methanol (3.75 ml.) and N,N-dimethylformamide (DMF) (1.25 ml.) was added, and the mixture was refluxed for 18 hours. The cooled mixture was diluted with ethyl acetate and DMF, and washed with water and brine, then dried (MgSO$_4$) and evaporated. The residue was triturated with 1:1 v/v ethyl acetate:ether to give methyl 4-[3-hydroxy-6-nitroindazol-1-ylmethyl]-3-methoxybenzoate (T) (0.158 g., 38%) as a yellow solid, m.p. 231°–235° C.

(b) Indazole (T) (1.68 g.) was added to a sodium (0.108 g.) in methanol (1.0 ml.). After stirring for 5 minutes, iodomethane (0.32 ml.) was added and stirring continued for 18 hours. The mixture was diluted with ethyl acetate, washed with water and brine, then dried (MgSO$_4$) and evaporated. The residue was purified by flash chromatography on silica gel (130 g.), eluting with 2:98 v/v ethyl acetate:dichloromethane to give methyl 4-[3-methoxy-6-nitroindazol-1-ylmethyl]-3-methoxybenzoate (U) (0.481 g., 28%) as a yellow solid, with satisfactory NMR spectral data.

(c) Palladium-on-carbon (5% w/w, 0.24 g.) was added to a solution of indazole (U) (0.48 g.) in ethyl acetate (25 ml.). The mixture was hydrogenated at 1.1 bars for 3 hours. The catalyst was removed by filtration through diatomaceous earth, and the filtrate evaporated. The residue was recrystallized from a hot ethyl acetate/petroleum ether mixture to give methyl 4-(6-amino-3-methoxyindazol-1-ylmethyl)-3-methoxybenzoate (S) (0.15 g., 34%), as a pale-yellow solid, m.p. 188°–193° C.

EXAMPLE 91

4-[6-(Cyclopentyloxycarbonyl)amino-3-methoxyindazol-1-ylmethyl]-3-methoxybenzoic Acid Using a similar procedure to that described in Example 9, except starting from methyl 4-[6-(cyclopentyloxycarbonyl)amino-3-methoxyindazol-1-ylmethyl]-3-methoxybenzoate, the title compound was obtained in 54% yield, as a solid, m.p. 199°–200.5° C.

EXAMPLE 93

N-[4-[6-(Cyclopentyloxycarbonyl)amino-3-methoxyindazol-1-ylmethyl]-3-methoxybenzoyl]benzenesulphonamide Using a similar procedure to that described in Example 57, except starting from the acid described in Example 91, the title compound was obtained in 53% yield, as a solid, m.p. 246°–247.5° C.

EXAMPLE 93

5-(2-Cyclopentylacetamido)-1-methyl-3-[4-(1-H-tetrazol-5-yl)-2-methoxybenzyl]indole Sodium hydroxide solution (1M, 1.9 ml.) and, second, palladium-on-carbon (10% w/w; 0.05 g.) were added to a solution of nitro-tetrazole (V) (0.69 g.) in methanol (50 ml.), and the mixture hydrogenated at an initial pressure of 3.3 bar. After two hours, catalyst was filtered off, washed with methanol, and the combined filtrate evaporated. The residue was dissolved in water (30 ml.), excess saturated aqueous dihydrogen sodium phosphate added, and the precipitate collected and dissolved in tetrahydrofuran (20 ml.). Charcoal was added, the solution heated and filtered through diatomaceous earth and the filter cake washed with tetrahydrofuran. The combined filtrate (which contained crude 5-amino-1-methyl-3-[2-methoxy-4-(1-H-tetrazol-5-yl)benzyl]indole) was added to a solution of 4-(dimethylamino)pyridine (0.244 g.), 1-(3-dimethylaminopropyl)-3-ethylcarbodiimide hydrochloride (0.384 g.) and cyclopentylacetic acid (0.256 g.) in dichloromethane (30 ml.). The mixture was stirred at ambient temperature for two days, the solvents evaporated, the residue partitioned between chloroform and water, the chloroform layer washed with water, dried (MgSO$_4$) and evaporated. The product was purified by flash chromatography on silica gel (using a 3 cm. diameter column) eluting with 70:30:4 v/v/v toluene: ethyl acetate:acetic acid, giving a product which was recrystallized from a mixture of methanol and water to give the title compound (hydrate) (0.064 g., 7.6%) as an off-white solid, m.p. 242°-243° C.

The starting nitro tetrazole (V) was itself prepared as follows:

(a) A solution of chlorosulphonyl isocyanate (5.35 ml.) in dichloromethane (3 ml.) was added over 45 minutes to a stirred suspension of 3-methoxy-4-methylbenzoic acid (9.97 g.) in dichloromethane (18 ml.) at reflux under an atomsphere of nitrogen. The resulting bright-red homogeneous solution was heated under reflux for 45 minutes, chilled in an ice-bath, and treated dropwise with N,N-dimethylformamide (9.5 ml.), over 15 minutes. After stirring for 30 minutes at 0° C., the orange solution was poured onto ice. The organic layer was separated, washed with water (5×20 ml.), dried (MgSO$_4$) and evaporated. The residue was purified by preparative HPLC (SiO$_2$, 10:90 v/v hexane: toluene) to give 3-methoxy-4-methylbenzonitrile (5.28 g., 60%) as a white solid, m.p. 51°-52.5° C.

(b) N-Bromosuccinimide (3.2 g.) and benzoyl peroxide (0.005 g.) were added to a solution of 3-methoxy-4-methylbenzonitrile (2.65 g.) in dry carbon tetrachloride (90 ml.). The mixture was heated to reflux for 15 minutes using a 250 watt tungsten lamp. The cooled reaction mixture was diluted with petrolum ether (b.p. 60°-80° C., 90 ml.), insoluble material removed by filtration, and the filtrate evaporated. The solid residue was recrystallized from a mixture of dichloromethane and petroleum ether to give 4-bromomethyl-3-methoxybenzonitrile (W) (2.64 g., 65%) as a white solid, m.p. 87°-91° C.

(c) An efficiently stirred mixture of 5-nitroindole (3.24 g.), bromide (W) (4.57 g.) and silver (I) oxide (4.87 g.) in dry dioxane (90 ml.) was heated at 100° C for 5 hours. Additional silver oxide (2 g.) was added, and heating continued for 1 hour. The cooled mixture was evaporated, the residue diluted with dichloromethane, filtered, washing the filter cake with dichloromethane until the washings were colorless, and the combined filtrate evaporated. The product was purified by flash chromatography on silica gel, eluting with 3:7 v/v ethyl acetate:hexane, giving a product which was crystallized from a mixture of ethyl acetate and hexane to give 3-(4-cyano-2-methoxybenzyl)-5-nitroindole (1.87 g., 30%) as a yellow powder, m.p. 204°-206° C.: partial NMR (80 MHz, DMSO-d$_6$): 3.92 (s,3 H, OMe); 4.12 (s,2 H, ArCH$_2$).

(d) Sodium hydride (60% w/w dispersion in mineral oil, 0.12 g.) was added to a stirred solution of 3-(4-cyano-2-methoxybenzyl)-5-nitroindole (0.85 g.) in dry N,N-dimethylformamide (10 ml.) under a nitrogen atmosphere. After about one hour, iodomethane (0.645 g.) was added dropwise, and stirring continued at ambient temperature for 5 hours. The mixture was poured onto saturated aqueous ammonium chloride solution, extracted with ethyl acetate (2×20 ml.), the extract washed with water, brine, dried (MgSO$_4$) and evaporated. The residue was crystallized from acetonitrile to give 3-(4-cyano-2-methoxybenzyl)-1-methyl-5-nitroindole (0.72 g., 81%) as a yellow solid, m.p. 200°-201° C., partial NMR (250 MHz, DMSO-d$_6$): 3.82 (s, 3 H, NMe); 3.92 (s,3 H, OMe); 4.12 (s,2 H, ArCH$_2$).

(e) A mixture of 3-(4-cyano-2-methoxybenzyl)-1-methyl-5-nitroindole (0.458 g.), sodium azide (0.741 g.), and triethylamine hydrochloride (0.785 g.) in dry N-methyl-2-pyrrolidinone (6 ml.), under nitrogen, was stirred and heated at 150° C. for 1.5 hours. The mixture was cooled to ambient temperature, 1N hydrochloric acid (25 ml.) added cautiously, while stirring, the precipitated solid isolated by filtration, washed with water and dried in vacuo to give 3-[2-methoxy-4-(1-H-tetrazol-5-yl)benzyl]-1-methyl-5nitroindole, (V) (0.484 g., 94%) as a yellow powder, m.p. 249°-250° C.: partial NMR (250 MHz, DMSO-d$_6$): 3.82 (s,3 H, NMe): 3.97 (s,3 H, OMe); 4.13 (s,2 H, ArCH$_2$).

EXAMPLE 94

Methyl 4-[5-(N'-Cyclopentylureido)-1-methylindol-3-ylmethyl]-3-methoxybenzoate A solution of trichloromethyl chloroformate (0.66 g.) in dry dioxan (10 ml.) was added over 10 minutes to a stirred solution of methyl 4-(5-amino-1-methylindol-3-ylmethyl)-3-methoxybenzoate (D) (1.09 g.) in dry dioxane (15 ml.) at ambient temperature. The reaction vessel was continuously purged with nitrogen gas, and the effluent bubbled through aqueous potassium hydroxide solution to destroy excess phosgene. The in situ formation of the isocyanate of (D) was followed by TLC. After 30 minutes cyclopentylamine (0.574 g.) was added, the mixture heated to 70° C. for 20 minutes, then cooled and diluted with water (100 ml.). The precipitate which formed was collected by filtration, dissolved in 95:5 v/v dichloromethane:methanol (100 ml.), and the solution washed with water, brine, dried (MgSO$_4$) and evaporated to give a solid which was recrystallized from acetonitrile to give the title compound (0.75 g., 56%) as a white solid, m.p. 210°-212° C.; partial NMR (250 MHz, DMSO-d$_6$): 1.25–1.80 (3 m, 8 H, cyclopentyl ring); 3.68 (s, 3 H, NMe); 3.83 (s,3 H, OMe); 3.90–4.0 (2 s+m,6 H, OMe, ArCH$_2$, —CHNH—); 5.93 (d, 1 H, —CH.NH—).

EXAMPLE 95

4-[5-(N-Cyclopentylureido)-1-methylindol-3-ylmethyl]-3-methoxybenzoic Acid

Using a similar procedure to that described in Example 9, except starting from the ester described in Example 94, the title compound was obtained in 70% yield as a white powder, m.p. 203°–206° C.

EXAMPLE 96

N-[4-[5-(N'-Cyclopentylureido)-1-methylindol-3-ylmethyl]-3-methoxybenzoyl]-2-methylbenzenesulphonamide Using a similar procedure to that described in Example 57, except using ortho-toluenesulphonamide and the acid described in Example 95, the title compound was obtained in 58% yield, as a white solid, m.p. 212°–215° C., (monohydrate).

EXAMPLE 97

Methyl 4-[5-(2-Cyclopentylacetamido)-1-(N,N-dimethylcarbamoylmethyl)indol-3-ylmethyl]-3-methoxybenzoate Using procedures similar to those described in Examples 47, 48 (see also Example 42), the title compound was obtained in 89% yield as a white powder, m.p. 129°–132° C.; partial NMR (250 MHz, DMSO-$d_6$): 1.15–1.30 (m,2 H, cyclopentyl ring); 1.45–1.80 (2 m,6 H, cyclopentyl ring); 2.25 (m,3 H, C$\underline{H}_2$CONH and —C$\underline{H}$CH$_2$); 2.83 (s,3 H, NMe); 3.06 (s,3 H, NMe); 3.83 (s,3 $\underline{H}$, OMe); 3.92 (s,3 H, OMe); 3.98 (s,2 H, ArC$\underline{H}_2$); 5.03 (s,2 H, NC$\underline{H}_2$); 9.61 (s,1 H, NH). The compound was made by starting from methyl 4-[5-amino-1-(N,N-dimethylcarbamoylmethyl)indol-3-ylmethyl]-3-methoxybenzoate (itself prepared by analogy with (D) in Example 4, that is by reaction of nitroindole derivative (C) with 2-chloro-N,N-dimethylacetamide in N,N-dimethylformamide in the presence of sodium hydride, followed by catalytic hydrogenation of the product).

EXAMPLE 98

Methyl 4-[1-(Tert-butoxycarbonylmethyl)-5-(2-cyclopentylacetamido)indol-3-ylmethyl]-3-methoxybenzoate Using a similar procedure to that described in Example 4, except using cyclopentylacetyl chloride, the title compound was obtained in 47% yield as a foam; partial NMR (DMSO-$d_6$): 1.1–1.3 (m,2 H, cyclopentyl ring); 1.40 [s,9 H, C(Me)$_3$]; 1.45–1.8 (2 m,6H, cyclopentyl ring): 2.25 (m,3 H, C$\underline{H}_2$CONH and —C$\underline{H}$CH$_2$); 3.83 (s, 3 H, OMe); 3.92 (s,3 $\underline{H}$, OMe); 3.98 (s,2 $\underline{H}$, ArC$\underline{H}_2$); 4.90 (s, 2 H, NC$\underline{H}_2$): 9.63 (s,1 H, NH). The compound was made by starting from methyl 4-[5-amino-1-(tert-butoxycarbonylmethyl)indol-3-ylmethyl]-3-methoxybenzoate (itself prepared by analogy with (D) in Example 4, that is by reaction with nitro-indole derivative (C) with tert-butyl bromoacetate in N,N-dimethylformamide in the presence of sodium hydride, followed by catalytic hydrogenation of the product).

EXAMPLE 99

Methyl 4-[1-(3-Cyanophenylmethyl)-5-(2-cyclopentylacetamido)indol-3-ylmethyl]-3-methoxybenzoate Using a similar procedure to that described in Example 4, except using cyclopentylacetyl chloride, the title compound was obtained in 30% yield as a yellow foam; partial NMR (DMSO-$d_6$): 1.05–1.3 (m,2 H, cyclopentyl ring); 1.4–1.8 (2 m,6 H, cyclopentyl ring); 2.24 (m,3 H, C$\underline{H}_2$CO and —C$\underline{H}$CH$_2$): 3.83 (s,3 H, OMe): 3.91 (s, 3 H, OMe): 4.0 (s,2 $\underline{H}$, ArC$\underline{H}_2$); 5.40 (s,2 H, NC$\underline{H}_2$): 9.63 (s, 1 H, NH). The compound was made by starting from methyl 4-[5-amino-1-(3-cyanophenylmethyl)indol-3-ylmethyl]-3-methylbenzoate (itself prepared by analogy with (D) in Example 4, that is by reaction of nitroindole derivative (C) with 3-cyanobenzyl bromide in N,N-dimethylformamide in the presence of sodium hydride, followed by catalytic hydrogenation (but using 5% w/w palladium-on-carbon as catalyst in 4:1 v/v tetrahydrofuran:methanol as solvent, and at atmospheric pressure) of the product.)

EXAMPLE 100

Methyl 4-[5-(2-Cyclopentylacetamido)-1-propargylindol-3-ylmethyl]-3-methoxybenzoate Using similar procedures to those described in Examples 4 and 23, the title compound was obtained in 60% yield, as a white solid, m.p. 160°–161° C.; partial NMR (250 MHz, DMSO-$d_6$): 1.1–1.3 (m,2 H, cyclopentyl ring); 1.45–1.8 (2 m,6 H, cyclopentyl ring); 2.26 (m,3 H, C$\underline{H}_2$CO and —C$\underline{H}$CH$_2$); 3.37 (t,1 H, ≡C—H); 3.83 (s,3 H, OMe): 3.92 (s,3 H, OMe): 3.98 (s,2 H, ArC$\underline{H}_2$); 4.99 (d,2 H, NC$\underline{H}_2$); 9.66 (s,1 H, NH). The title compound was made by starting from methyl 4-(5-amino-1-propargylindol-3-ylmethyl)-3-methoxybenzoate (itself prepared by analogy with (F) in Example 23, that is by reaction of nitroindole derivative (C) with propargyl bromide in N,N-dimethylformamide in the presence of sodium hydride, followed by stannous chloride reduction of the product.)

EXAMPLES 101–104

Using a similar procedure to that described in Example 9, except using the esters described in Examples 97–100, the following acids of formula 1 in which W is a direct link to R$^1$ were obtained by hydrolysis of the corresponding methyl esters:

| Ex. | R$^1$ | Rd | m.p. (°C.) | yield (%) |
|---|---|---|---|---|
| 101 | cyclopentylmethyl | N,N-dimethylcarbamoylmethyl | 223–226* | 54 |
| 102 | cyclopentylmethyl | carboxymethyl # | 256–258 | 74 |
| 103 | cyclopentylmethyl | 3-cyanophenylmethyl | 130–132* | 89 |
| 104 | cyclopentylmethyl | propargyl | 226–227* | 87 |

*Isolated as a partial hydrate.
Hydrolyses of both methyl and tert-butyl esters.

EXAMPLE 105

N-[4-[5-(Cyclopentyloxycarbonyl)amino-1-methylindol-3-ylmethyl]-3-methoxybenzoyl]-2-methylbenzenesulphonamide Using a similar procedure to that described in Example 57, except using ortho-toluenesulphonamide and the acid described in Example 9, the title compound was obtained in 69% yield, as a white solid, m.p 138°-140° C.

Analysis calculated for:
$C_{31}H_{33}N_3O_6S$: C, 64.68; H, 5.78; N, 7.30.
Found: C, 64.49: H, 5.78: N, 7.21.

EXAMPLE 106

4-(6-Hexanamido-2,3-dihydrobenz-1,4-oxazin-4-ylmethyl)-3-hydroxybenzoic Acid

Lithium thioethoxide was prepared by the dropwise addition of n-butyllithium (4 ml. of 1.53 molar solution in hexane) to a stirred solution of ethyl mercaptan (0.5 ml.) in dry N,N'-dimethylpropylene urea (DMPU) (9 ml.), under a nitrogen atmosphere. A solution of methyl 4-(6-hexanamido-2,3-dihydrobenz-1,4-oxazin-4-ylmethyl)-3-methoxybenzoate (prepared as described in Example 26) (0.35 g.) in DMPU (3 ml.) was added, the mixture stirred at ambient temperature for 15 minutes, then heated to, and maintained at, 130° C. for 4 hours. The cooled mixture was diluted with water, acidified with acetic acid, extracted with ethyl acetate, the extracts washed with water, dried (MgSO₄) and evaporated. The product was purified by flash chromatography on silica gel, eluting with 80:20:2 v/v/v toluene:ethyl acetate:acetic acid, giving a white solid which was washed with hexane and dried, to give the title compound (0.114 g., 36%) as a white solid, m.p. 183°-184° C.

EXAMPLE 107

Methyl 3(6-Hexanamido-2,3-dihydrobenz-1,4-oxazin-4-ylmethyl)benzoate

Hexanoyl chloride (0.135 g.) was added dropwise to a stirred solution of methyl 3-(6-amino-2,3-dihydrobenz-1,4-oxazin-4-ylmethyl)benzoate (X) (0.3 g.), and N-methylmorpholine (0.101 g.) in dichloromethane (30 ml.). After 0.5 hours, the mixture was diluted with dichloromethane, washed with water, dried (MgSO₄) and evaporated to give an oil which was filtered through a short column of silica gel using 35:65 v/v ethyl acetate:hexane to give the title compound as a syrup: partial NMR (80 MHz, CDCl₃): 0.8-1.9 [complex m,9 H, CH₃(CH₂)₃]; 2.2 (m,2 H, C$\underline{H}$₂CONH); 3.3 (m,2 H, N.C$\underline{H}$₂.CH₂.O; 3.9 (s,3 H, OMe); 4.2 (m,2 H, N.CH₂.C$\underline{H}$₂O); 4.5 (s,2 H, N.C$\underline{H}$₂Ar).

The amino ester (X) was obtained as follows:

(a) A mixture of 6-nitro-2,3-dihydrobenz-1,4-oxazine (0.45 g.), methyl 3-bromomethylbenzoate* (Y) (0.58 g.), potassium carbonate (0.35 g.), and sodium iodide (0.38 g.) in dry 2-butanone (25 ml.) was stirred and heated under reflux for 48 hours. The cooled reaction mixture was filtered, the filter cake washed with 2-butanone, and the combined filtrate evaporated. The product was purified by flash chromatography on silica gel, eluting with 5:95 v/v ethyl acetate:toluene to give methyl 3-(6-nitro-2,3-dihydrobenz-1,4-oxazin-4-ylmethyl)benzoate (0.7 g., 85%) as a yellow oil; partial NMR (80 MHz, CDCl₃) 3.5 (m,2 H, N.C$\underline{H}$₂.CH₂O); 3.9 (s,3 H, OMe); 4.3 (m,2 H, N.CH₂.C$\underline{H}$₂O); 4.6 (s,2 H, NCH₂Ar).

*Methyl 3-bromomethylbenzoate (Y) was prepared from methyl 3-methylbenzoate by bromination using N-bromosuccinimide in an analogous manner to that used to prepare 4-bromomethyl-3-methoxybenzonitrile (W) as described in part (b) of Example 93.

(b) A mixture of methyl 3-(6-nitro-2,3-dihydrobenz-1,4-oxazin-4-ylmethyl)benzoate (0.65 g.) and palladium-on-carbon (10% w/w, 0.025 g.) in ethyl acetate (40 ml.) was hydrogenated at an initial pressure of 2.9 bar. The catalyst was removed by filtration through diatomaceous earth, washing the filter cake with ethyl acetate, and the filtrate was evaporated to give methyl 3-(6-amino-2,3-dihydrobenz-1,4-oxazin-4-ylmethyl)benzoate (X) (0.3 g., 51%) as a gum; partial NMR (80 MHz, CDCl₃): 3.3 (m,2 H, N.C$\underline{H}$₂CH₂.O); 3.9 (s,3 H, OMe); 4.15 (m,2 H, N.CH₂.C$\underline{H}$₂.$\overline{O}$); 4.5 (s,2 H, NC$\underline{H}$₂Ar).

EXAMPLE 108

3-(6-Hexanamido-2,3-dihydrobenz-1,4-oxazin-4-ylmethyl)benzoic Acid

Lithium hydroxide monohydrate (0.2 g.) in water (5 ml.) was added to a stirred solution of methyl 3-(6-hexanamido-2,3-dihydrobenz-1,4-oxazin-4-ylmethyl)benzoate (ca. 400 mg.) in 1:1 v/v methanol: tetrahydrofuran (10 ml.). When TLC (solvent system 80:20:2 v/v/v toluene:ethyl acetate:acetic acid) indicated complete disappearance of ester, the mixture was diluted with water, filtered to remove any solids, and carefully acidified with 1N hydrochloric acid. The precipitate was isolated by filtration and recrystallized from a mixture of methanol and water to give the title compound (0.176 g., 46% overall yield from amino ester (X)) as an off-white solid, m.p. 167°-171° C. (hemihydrate).

EXAMPLE 109

N-[4-[5-(2-Cyclopentylacetamido)-1-(N,N-dimethylcarbamoylmethyl)indol-3-ylmethyl]-3-methoxybenzoyl]-2-methylbenzenesulphonamide Using a similar procedure to that described in Example 57, except using ortho-toluenesulphonamide and the acid described in Example 101, the title compound was obtained in 79% yield, as a white solid, m.p. 215°-217.5° C. (hemihydrate).

Analysis calculated for:
$C_{35}H_{40}N_4O_6S.0.5H_2O$: C, 64.30; H, 6.32; N, 8.57.
Found: C, 64.38; H, 6.28; N, 8.55.

EXAMPLE 110

4-[1-Acetyl-5-(2-cyclopentylacetamido)indol-3-ylmethyl]-3-methoxybenzoic Acid

A solution of 4-(1-acetyl-5-aminoindol-3-ylmethyl)-3-methoxybenzoic acid (Z) (0.31 g.), cyclopentylacetic acid (0.117 g.), 4-(dimethylamino)pyridine (0.233 g.) and 1-(3-dimethylaminopropyl)-3-ethylcarbodiimide hydrochloride (0.35 g.) in dichloromethane (20 ml.), under a nitrogen atmosphere, was stirred at ambient temperature for two hours. The mixture was acidified with hydrochloric acid (1N, 30 ml.), extracted with ethyl acetate (3×50 ml.), and the combined extracts dried (MgSO₄) and evaporated. The residual oil was purified by flash chromatography on silica gel (100 ml.), eluting with 50:45:5 v/v/v hexane:dichloromethane:ethyl acetate, to give a product which was recrystallized from a mixture of tetrahydrofuran and ether, and then from a mixture of ethanol and water, to give the title compound (0.055 g., 14%), as a white solid, m.p. 245°-247° C.

The starting amino acid (Z) was itself prepared as follows from nitro ester (C):

(a) A solution of lithium hydroxide monohydrate (1.2 g.) in water (20 ml.) was added to a suspension of nitro ester (C) (2.0 g.) in methanol (30 ml.). The mixture was stirred at ambient temperature for 18 hours and then acidified with hydrochloric acid (1N, 50 ml.). The yellow precipitate was isolated by filtration, washed with water, and dried to give 4-(5-nitroindol-3-ylmethyl)-3-methoxybenzoic acid; partial NMR (250 MHz, DMSO-$d_6$): 3.92 (s,3 H, OMe); 4.12 (s,2 H, ArC$\underline{H}_2$): 11.64 (br s,1 H, NH).

(b) A solution of 4-(5-nitroindol-3-ylmethyl)-3-methoxybenzoic acid (0.6 g.) in N,N-dimethylformamide (DMF), (3 ml.) was added to a stirred suspension of oil-free sodium hydride (0.088 g.) in DMF (8 ml.) under a nitrogen atmosphere at ambient temperature. The red solution was stirred for 20 minutes, and acetic anhydride (0.187 g.) added. After 1 hour, the mixture was poured into hydrochloric acid (1N, 30 ml.), extracted with ethyl acetate (3×50 ml), the combined extracts washed with water (2×20 ml.), brine, dried (MgSO$_4$) and evaporated. The product was crystallized from a mixture of tetrahydrofuran and ether to give 4-(1-acetyl-5-nitroindol-3-ylmethyl)-3-methoxybenzoic acid (0.455 g., 67%) as a yellow powder; partial NMR (250 MHz, DMSO-$d_6$): 2.68 (s,3 H, NCOC$\underline{H}_3$); 3.95 (s,3 H, OMe); 4.13 (s,2 H, ArC$\underline{H}_3$).

(c) Palladium-on-carbon (10% w/w, 0.1 g.) was added to a solution of 4-(1-acetyl-5-nitroindol-3-ylmethyl)-3-methoxybenzoic acid (0.35 g.) in a mixture of 1:1 v/v methanol:tetrahydrofuran (50 ml.), which solution had been deoxygenated by passing a stream of nitrogen gas through it, and the mixture hydrogenated at an initial pressure of 50 psi. After 24 hours, the catalyst was removed by filtration through diatomaceous earth, and the filtrate evaporated to give 4-(1-acetyl-5-aminoindol-3-ylmethyl)-3-methoxybenzoic acid (Z) (0.31 g., 91%); partial NMR (250 MHz, CD$_3$OD): 2.53 (s,3 H, NCOC$\underline{H}_3$); 3.94 (s,3 H, OMe); 4.00 (s,2 H, ArC$\underline{H}_2$).

EXAMPLE 111

Calcium N-[4-[5-(cyclopentyloxycarbonyl)amino-1-methylindol-3-ylmethyl]-3-methoxybenzoyl]-2-methylbenzenesulphonamide Calcium oxide (0.0487 g.), and distilled water (10 ml.) were added sequentially to a solution of N-[4-[5-(cyclopentyloxycarbonyl)amino-1-methylindol-3-ylmethyl]-3-methoxybenzoyl]-2-methylbenzenesulphonamide (1.0 g.) in tetrahydrofuran (THF), (8 ml.). The turbid solution was heated at 50° C. for 20-25 minutes, and the cooled, clear, two-phase mixture evaporated (at about 50° C.). The residue was redissolved in THF (20 ml.), the solution filtered through a pad of diatomaceous earth, washing the filter cake with a little THF, the filtrate added dropwise to stirred ether (175 ml.), and the resulting solution added dropwise to stirred ether (300 ml.). The precipitate was collected by filtration. The filtrate was evaporated, redissolved in THF (3.5 ml.) and added dropwise to stirred ether (150 ml.). The precipitate was collected, combined with the first precipitate and dried to give the title compound (0.865 g., 84%) as a white solid, and a partial hydrate, m.p. 220° C. (approximately).

Analysis calculated for $C_{62}H_{64}N_6O_{12}S_2Ca.0.75H_2O$: C, 61.91; H, 5.49; N, 6.99.

Found: C, 61.83; H, 5.49; N, 6.87.

EXAMPLE 112

Methyl 4-[5-(cyclopentyloxycarbonyl)amino-1-methylindol-3-ylmethyl]-3-methoxybenzoate A solution of 5-(cyclopentyloxycarbonyl)amino-1-methylindole (AA) (1.3 g.) and methyl 4-bromomethyl-3-methoxybenzoate (B) (1.3 g.) in N,N-dimethylformamide (25 ml.) was stirred and heated at 100° C., under a nitrogen atmosphere, while protecting the reaction vessel from light with aluminum foil, for 24 hours. The cooled mixture was poured onto saturated aqueous sodium bicarbonate solution (300 ml.), extracted with ethyl acetate (3×100 ml.), the combined extracts washed with brine (50 ml.), dried (MgSO$_4$), and evaporated. The product was isolated by flash chromatography on silica gel (3.5 cm. diameter column) to give the title compound (P) (0.98 g., 45%), identical with that obtained in Example 8.

The starting cyclopentyl urethane (AA) was prepared from 5-nitroindole by methylation (using sodium hydride in N,N-dimethylformamide) followed by catalytic reduction of the nitro compound to the corresponding amino compound, and acylation of the amino compound using cyclopentyl chloroformate (using methods similar to those described in Example 1, part (b), and in Example 3).

EXAMPLE 113

Methyl 4-[6-(2-Cyclopentylacetamido)benzotriazol-1-ylmethyl]-3-methoxybenzoate

Using a similar procedure to that described in Example 47, except starting from the amino-ester (M), the title compound was obtained in 58% yield as a white powder, m.p. 206°-208° C.

EXAMPLE 114

4-[6-(2-Cyclopentylacetamido)benzotriazol-1-ylmethyl]-3-methoxybenzoic Acid

Using a procedure similar to that described in Example 29, except starting from the ester described in Example 113, the title compound was obtained as a white powder in 98% yield, m.p. 235°-238° C., as a partial hydrochloride salt.

EXAMPLE 115

N-[4-[6-(2-Cyclopentylacetamido)benzotriazol-1-ylmethyl]-3-methoxybenzoyl]benzenesulphonamide Using a similar procedure to that described in Example 32, except starting from the acid described in Example 114, and recrystallizing from a mixture of methanol and water, the title compound was obtained in 95% yield as a white powder, m.p. 211°-213° C., as a partial hydrate.

EXAMPLE 116

Methyl 4-[6-(2-Cyclopentylacetamido)-3-hydroxyindazol-1-ylmethyl]-3-methoxybenzoate A mixture of methyl 4-[3-benzyloxy-6-(2-cyclopentylacetamido)indazol-1-ylmethyl]-3-methoxybenzoate (BB) (5.0 g.), and palladium-on-carbon (5% w/w, 1.25 g.), in ethyl acetate (190 ml.), was hydrogenated at 1.1 bar for 7.5 hours. The catalyst was removed by filtration through diatomaceous earth, washing the filter cake with ethanol, the filtrate partially evaporated, and the residue allowed to crystallize to give the title compound (2.56 g., 62%), as a solid, m.p. 242°–245° C.

The ester (BB) was itself obtained as follows:

(a) Methyl 4-(3-hydroxy-6-nitroindazol-1-ylmethyl)-3-methoxybenzoate (T) (35.7 g.) was added to a mixture of sodium (2.3 g.) and methanol (200 ml.). The mixture was stirred for 18 hours, and evaporated. The residue was dissolved in N,N-dimethylformamide (100 ml.), cooled to 0° C., and benzyl bromide (15.5 ml.) added. After 18 hours at ambient temperature, ethyl acetate and 1N sodium hydroxide solution were added. The precipitate was isolated by filtration, washed with ether, and chromatographed by HPLC on silica gel, eluting with dichloromethane, to give methyl 4-(3-benzyloxy-6-nitroindazol-1-ylmethyl)-3-methoxybenzoate (CC) (27 g., 60%) as a solid; NMR (250 MHz, DMSO-$d_6$): 3.84 (s,3 H, OMe); 3.86 (s,3 H, OMe); 5.38 (s,2 H, NCH$_2$); 5.65 (s,2 H, OCH$_2$); 6.95 (d,1 H); 7.36 (m,3 H); 7.46 (m,5 H): 7.86 (m,2 H); 8.66 (s,1 H).

(b) Zinc dust (0.065 g.) was added to a stirred mixture of methyl 4-(3-benzyloxy-6-nitroindazol-1-ylmethyl)-3-methoxybenzoate (CC) (0.043 g.) and acetic acid (0.9 ml.). The mixture was stirred for 2 hours, diluted with ether, and filtered. The filtrate was washed with water, brine, dried (MgSO$_4$), and evaporated to give methyl 4-(6-amino-3-benzyloxyindazol-1-ylmethyl)-3-methoxybenzoate (DD) (0.034 g., 85%) as a brown oil, and was used without further purification as described below.

(c) Using a similar procedure to that described in Example 47, except starting from amino ester (DD), there was obtained methyl 4-[3-benzyloxy-6-(2-cyclopentylacetamido)indazol-1-ylmethyl]-3-methoxybenzoate (BB) in 32% yield, as a solid, m.p. 139°–140° C.

EXAMPLE 117

4-[6-(2-Cyclopentylacetamido)-3-hydroxyindazol-1-ylmethyl]-3-methoxybenzoic Acid Using a similar procedure to that described in Example 9, but starting from methyl 4-[6-(2-cyclopentylacetamido)-3-hydroxyindazol-1-ylmethyl]-3-methoxybenzoate, a crude product was obtained which was purified by flash chromatography on silica gel (40 g.), eluting with 3:7 v/v methanol:dichloromethane. The chromatogaphed product was suspended in a mixture of ethyl acetate and tetrahydrofuran and washed with 1N hydrochloric acid, water, and brine, dried (MgSO$_4$), evaporated and recrystallized from a mixture of methanol, dichloromethane, and petroleum ether to give the title compound in 16% yield as a solid, m.p. 269°–272° C. as a partial hydrate.

EXAMPLE 118

Methyl 4-[6-(2-Cyclopentylacetamido)-3-(N-ethylcarbamoylmethoxy)indazol-1-ylmethyl]-3-methoxybenzoate Using a similar procedure to that described in Example 42, except starting from methyl 4-[6-(2-cyclopentylacetamido)-3-hydroxyindazol-1-ylmethyl]-3-methoxybenzoate (that is reaction of this compound with 2-chloro-N-ethylacetamide in N,N-dimethylformamide in the presence of sodium hydride), and flash chromatography of the crude product on silica gel (75 g.), eluting with 1:1 v/v ethyl acetate:dichloromethane, the title compound was obtained in 34% yield as a solid, m.p. 178°–181° C.

EXAMPLE 119

4-[6-(2-Cyclopentylacetamido)-3-(N-ethylcarbamoylmethoxy)indazol-1-ylmethyl-3-methoxybenzoic Acid Using a similar procedure to that described in Example 9, except using the ester from Example 118, the title compound was obtained in 80% yield, as a solid, m.p. 219°–221° C.

EXAMPLE 120

Methyl 4-[5-(Hexanamido)-1-(methoxycarbonylmethyl)indol-3-ylmethyl]-3-methoxybenzoate Using a similar procedure to that described in Example 4 (see also Example 98), the title compound was isolated in 86% yield, as an oil; partial NMR (250 MHz, DMSO-$d_6$): 0.87 (t,3 H, CH$_2$.CH$_3$); 1.26–1.30 (m,4 H); 1.50–1.60 (m,2 H): 2.25 (t,2 H, $\overline{\text{CH}}_2$CON); 3.66 (s,3 H, OMe); 3.83 (s,3 H, OMe); 3.92 (s,3 $\overline{\text{H}}$, OMe); 3.98 (s,2 H, ArCH$_2$Ar); 5.04 (s,2 H, NCH$_2$); 9.66 (s,1 H, NH); starting from 4-[5-amino-1-(methoxycarbonylmethyl)indol-3-ylmethyl]-3-methoxybenzoate (itself prepared by analogy with (D) in Example 4, that is by reaction of nitroindole derivative (C) with methyl bromoacetate, except in tetrahydrofuran, in the presence of sodium hydride, followed by catalytic hydrogenation of the product).

EXAMPLE 121

4-[1-Carboxymethyl-5-(hexanamido)indol-3-ylmethyl]-3-methoxybenzoic Acid

Using a procedure similar to that described in Example 9, except starting from the ester described in Example 120, the title compound was obtained in 59% yield, as a white solid, m.p. 235°–240° C.

EXAMPLE 122

N-[4-[6-(2-Cyclopentylacetamido)-3-(N-ethylcarbamoylmethoxy)indazol-1-ylmethyl]-3-methoxybenzoyl]-2-methylbenzenesulphonamide Using a similar procedure to that described in Example 57, except using ortho-toluenesulphonamide and the acid described in Example 119, the title compound was obtained as a partial hydrate in 32% yield as a solid, m.p. 222°–223.5° C.

Analysis calculated for:
C$_{34}$H$_{39}$N$_5$O$_7$S.0.75H$_2$O: C, 60.47: H, 6.04; N, 10.37.
Found: C, 60.41; H, 5.83; N, 10.31.

EXAMPLE 123

Methyl 4-[5-(2-Cyclopentylacetamido)indol-3-ylmethyl]-3-methoxybenzoate

Starting from amino-ester (A), and using a similar procedure to that described in Example 4, except using cyclopentylacetyl chloride (see also Example 98), the title compound was obtained in quantitative yield as a foam; partial NMR (250 MHz, DMSO-$d_6$): 1.2–1.8 (3 m,8 H, cyclopentyl ring); 2.24 (m,3 H, CH$_2$CONH and —CHCH$_2$); 3.893 (s,3 H, OMe); 3.93 (s,3 $\overline{\text{H}}$, OMe); 3.99 (br s,2 H, CH$_2$Ar); 9.57 (br s,1 H, NCHO); 10.79 (br d,1 H, —NH—).

EXAMPLE 124

4-[5-(2-Cyclopentylacetamido)indol-3-ylmethyl]-3-methoxybenzoic Acid

Using a similar procedure to that described in Example 9, except starting from the ester described in Example 123, the title compound was obtained in 83% yield as a white solid, m.p. 218°–219° C.

EXAMPLE 125

N-[4-[5-(2-Cyclopentylacetamido)indol-3-ylmethyl]-3-methoxybenzoyl]-2-methylbenzenesulphonamide Using a similar procedure to that described in Example 57, except starting from ortho-toluenesulphonamide and the acid described in Example 124, the title compound was obtained in 56% yield as white powder, m.p. 248°–250° C.

EXAMPLE 126

Methyl 4-[6-(2-Cyclopentylacetamido)-3-oxo-2-propyl-2H,3H-indazol-1-ylmethyl]-3-methoxybenzoate Palladium-on-carbon (5% w/w, 0.095 g.) was added to a solution of methyl 4-[2-allyl-6-(2-cyclopentylacetamido)-3-oxo-2H,3H-indazol-1-ylmethyl]-3-methoxybenzoate (0.462 g.) in ethyl acetate (20 ml.). The mixture was hydrogenated at 1.1 bar for 5 hours. The catalyst was removed by filtration through diatomaceous earth, the filtrate evaporated and the residue purified by flash chromatography on silica gel (40 g.), eluting with 1:3:7 v/v/v acetic acid:ethyl acetate:dichloromethane. The chromatographed product was dissolved in acetone and toluene, and the solution evaporated to give the title compound in 84% yield, as a solid glass, m.p. 74.5°–77° C.

The starting ester methyl 4-[2-allyl-6-(2-cyclopentylacetamido)-3-oxo-2H,3H, indazol-1-ylmethyl]-3-methoxybenzoate was itself prepared as follows. Using a similar procedure to that described in Example 42, except starting from methyl 4-[6-(2-cyclopentylacetamido)-3-hydroxyindazol-1-ylmethyl]-3-methoxybenzoate (that is, reaction of this compound with allyl bromide in N,N-dimethylformamide in the presence of sodium hydride), a mixture of methyl 4-[2-allyl-6-(2-cyclopentylacetamido)3-oxo-2H,3H-indazol-1-ylmethyl]-3-methoxybenzoate, and methyl 4-[3-allyloxy-6-(2-0 cyclopentylacetamido)indazol-1-ylmethyl]-3-methoxybenzoate was obtained. The mixture of compounds was heated neat at 200° C. for 18 hours, and the product isolated by flash chromatography on silica gel (60 g.), eluting with 1:30:70 v/v/v acetic acid:ethyl acetate:dichloromethane, to give methyl 4-[2-allyl-6-(2-cyclopentylacetamido)-3-oxo-2 H,3 H-indazol-1-ylmethyl]-3-methoxybenzoate in 81% yield, as an oil with satisfactory NMR spectral data.

EXAMPLE 127

4-[6-(2-Cyclopentylacetamido)-3-oxo-2-propyl-2H,3H-indazol-1-ylmethyl]-3-methoxybenzoic Acid Using a similar Procedure to that described in Example 9, except starting from methyl 4-[6-(2-cyclopentylacetamido)-3-oxo-2-propyl-2H,3H-indazol-1-ylmethyl]-3-methoxybenzoate the title compound was obtained in 83% yield as a solid, m.p. 122.5°–125° C.

EXAMPLE 128

The following illustrates representative pharmaceutical dosages forms which may be used for the therapeutic or prophylactic administration of an acidic compound of formula I (that is, M is an acidic group as defined hereinbefore) or of a pharmaceutically acceptable salt thereof (hereinafter referred to as Compound 'X'):

| (i) | Tablet 1 | mg/tablet |
|---|---|---|
| | 'Compound X' | 100 |
| | Lactose | 182.75 |
| | Croscarmellose Sodium | 12.0 |
| | Starch | 2.25 |
| | Magnesium stearate | 3.0 |
| (ii) | Tablet 2 | mg/tablet |
| | 'Compound X' | 20 |
| | Microcrystalline cellulose | 420 |
| | Polyvinylpyrrolidone | 14.0 |
| | Starch | 43.0 |
| | Magnesium stearate | 3.0 |
| (iii) | Capsule | mg/capsule |
| | 'Compound X' | 10 mg. |
| | Lactose | 488.5 |
| | Magnesium stearate | 1.5 |
| (iv) | Injection 1 | (10 mg./ml.) |
| | 'Compound X' (free acid form) | 1.0% w/v |
| | Sodium phosphate | 3.6% w/v |
| | 0.1M Sodium hydroxide solution | 15.0% w/v |
| | Water for injection ... to 100% | |
| (v) | Injection 2 (buffered to pH 6) | (1 mg./ml.) |
| | 'Compound X' (free acid form) | 0.1% w/v |
| | Sodium phosphate | 2.26% w/v |
| | Citric acid | 0.38% w/v |
| | Polyethylene glycol 400 | 3.5% w/v |
| | Water for injection ... to 100% | |
| (vi) | Aerosol | mg./ml. |
| | 'Compound X' | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

It will be appreciated that the above pharmaceutical compositions may be varied according to well known pharmaceutical techniques to accommodate differing amounts and types of active ingredient 'Compound X'. The aerosol (vi) may be used in conjunction with a standard, metered dose aerosol dispenser.

What is claimed is:

1. A compound of formula I

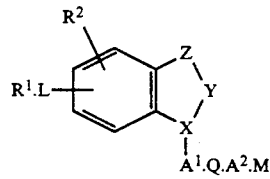

wherein the group >X—Y—Z— is selected from the group consisting of:
 (c) >C=CRa—Zb—
 (d) >N—CRa=N—
 (f) >N—N=N—
 (g) >N—NRg—CO—
 (h) >N—N=C.ORd— wherein

Ra is hydrogen or (1–4C)alkyl;

Rd is hydrogen or (1–10C) alkyl optionally containing one or two double or triple bonds and in which a carbon atom may optionally be replaced by oxygen or sulphur, said (1–10C)alkyl additionally optionally bearing a substituent selected from the group consisting of (1–4C)alkoxy, cyano, carboxy, 1H-tetrazol-5-yl, carbamoyl, N-1–4C)carbamoyl, [N,N-di[(1–4C)alkyl]carbamoyl] N,N-di{(1–4C)alkyl}carbamoyl, and (1–4C)alkoxycarbonyl, or Rd is selected from the group consisting of (3–8C)cycloalkyl, (3–8C)cycloalkyl-(1–4C)alkyl, (2–6C)alkanoyl and phenyl-(1–4C)alkyl, the phenyl moiety of which may optionally bear a substituent selected from the group consisting of cyano, halogeno, (1–4C)alkyl, (1–4C)alkoxy and trifluoromethyl;

Rg is (1–4C)alkyl;

Zb is oxy or thio;

the group $R^1.L—$ stands for amidic radicals of the formula: $R^1.W.CO.NH—$ or $R^1.W.CS.NH—$, in which $R^1$ is selected from the group consisting of (a) (2–10C)alkyl optionally containing 1 or more fluorine substituents; (b) phenyl-(1–6C)alkyl in which the (1–6C)alkyl moiety may optionally bear a fluoro or (1–4C)alkoxy substituent and in which the phenyl moiety may optionally bear a substituent selected from the group consisting of halogeno, (1–4C)alkyl, (1–4C)alkoxy and trifluoromethyl; and (c) (3–8C)cycloalkyl or (3–8C)cycloalkyl-(1–6C)alkyl, the cyclic moiety of any of which optionally may contain one unsaturated linkage and may optionally bear 1 or 2 (1–4C)alkyl substituents;

W is oxy, thio, imino or a direct link to $R^1$;

$R^2$ is hydrogen, halogeno, (1–4C)alkyl or (1–4C)alkoxy;

Q is phenylene optionally bearing 1 or more substituents independently selected from the group consisting of halogeno, hydroxy, (1–4C)alkyl, (1–4C) alkoxy and trifluoromethyl;

$A^1$ is (1–2C)alkylene or vinylene;

$A^2$ is methylene, vinylene or a direct link to M; and

M is an acidic group selected from the group consisting of carboxy, 1H-tetrazol-5-yl and an acylsulphonamide residue of the formula $—CO.NH.SO_mR^3$ in which m is the integer 1 or 1 and $R^3$ is selected from the group consisting of (1–6C)alkyl, (3–8C)cycloalkyl, (6–12C)aryl, heteroaryl comprising 5–12 atoms at least one of which is carbon and at least one of which is selected from a group consisting of oxygen, sulfur and nitrogen, and (6–12C)aryl-(1–4C)alkyl, in any of which the aromatic or heteroaromatic moiety may bear 1 or 2 substituents selected from the group consisting of halogeno, (1–4C)alkyl, (1–4C)alkoxy, trifluoromethyl, nitro and amino;

or a pharmaceutically acceptable salt thereof.

2. A compound as claimed in claim 1 wherein $R^1$ is selected from the group consisting of ethyl, propyl, isopropyl, butyl, isobutyl, sec-butyl, t-butyl, pentyl, 1-ethylpropyl, hexyl, heptyl, 1-ethylpentyl, nonyl, heptafluoropropyl, benzyl, 4-chlorobenzyl, 4-trifluoromethylbenzyl, 4-methylbenzyul, 1-phenylethyl, 2-phenylethyl, 1-methyl-1-phenylethyl, 1-phenylpropyl, 1-phenylpentyl, alpha-fluorobenzyl, alpha-methoxybenzyl, cyclobutyl, cyclopentyl, cyclohexyl, cyclopentylmethyl, cyclohexylmethyl, 2-cyclopentylethyl, 1-cyclopentylbutyl, 1-cyclohexylpropyl, 1-cyclohexylbutyl, 5-methyl-2-(1-methylethyl)cyclohexyl, and 1-cyclohexen-4-yl;

$R^2$ is selected from the group consisting of hydrogen, fluoro, chloro, bromo, methyl and methoxy;

$R^3$ is selected from the group consisting of methyl, isopropyl, butyl, cyclopentyl, phenyl, 4-chlorophenyl, 4-methylphenyl, 2-methylphenyl, naphthyl, thien-2-yl and 6-chloropyrid-3-yl;

Ra is selected from hydrogen and methyl;

Rd is selected from the group consisting of hydrogen, methyl, ethyl, propyl, butyl, pentyl, hexyl, allyl, propargyl, 3-methylbutyl, 3-methylbut-2-enyl, 2-carbamoylethyl, carboxymethyl, carboxyethyl, N-ethylcarbamoylmethyl, N,N-dimethylcarbamoylmethyl, 2-carboxyvinyl, 2-(methoxycarbonyl)vinyl, 2-methoxyethyl, 3-methoxypropyl, cyclopentyl, cyclopropylmethyl, acetyl, benzyl, 3-cyanobenzyl and 4-chlorobenzyl;

Rg is selected from the group consisting of methyl, ethyl, and propyl;

$A^1$ is selected from methylene and ethylene;

$A^2$ is selected from a direct linkage and methylene;

Q is selected from the group consisting of m-phenylene and p-phenylene, each of which optionally may bear a fluoro, chloro, hydroxy, methyl, methoxy or trifluoromethyl substituent; and W is selected from the group consisting of oxy, imino, thio and a direct linkage.

3. A compound as claimed in claim 2 wherein $R^1$ is selected from the group consisting of butyl, pentyl, 1-ethylpentyl, 1-phenylpropyl, alpha-fluorobenzyl, alpha-methoxybenzyl, cyclopentyl, and cyclopentylmethyl;

$R^2$ is hydrogen;

$R^3$ is phenyl or 2-methylphenyl;

Ra is hydrogen;

Rd is selected from the group consisting of hydrogen, methyl, ethyl, propyl, hexyl, allyl, propargyl, 3-methylbutyl, 3-methylbut-2-enyl, carboxymethyl, carboxyethyl, N-ethylcarbamoylmethyl, N,N-dimethylcarbamoylmethyl, 2-methoxyethyl, cyclopentyl, cyclopropylmethyl, acetyl, benzyl, and 3-cyanobenzyl;

Rg is propyl, $A^1$ is methylene;

$A^2$ is a direct link;

Q is selected from the group consisting of m-phenylene and p-phenylene, each of which may optionally be substituted by a hydroxy or methoxy; and W is selected from the group consisting of oxy, imino and a direct linkage.

4. A compound as claimed in claim 1 selected from the group consisting of benzo[b]thiophenes of formula Ic

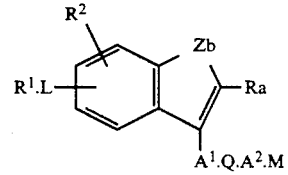

wherein Zb is thio, benzimidazoles of formula Id,

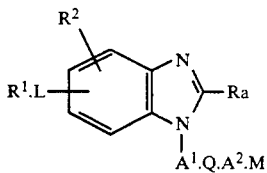

benzotriazoles of formula If,

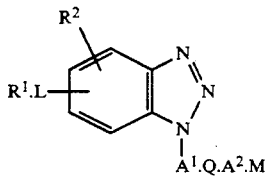

indazolones of formula of formula Ig,

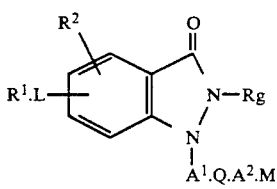

and
indazoles of formula Ih,

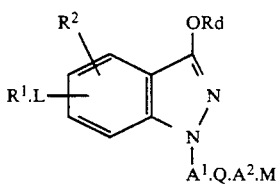

or a pharmaceutically acceptable salt thereof.

5. A compound as claimed in claim 1 selected from the group consisting of
benzo[b]thiophene derivatives of formula IIc,

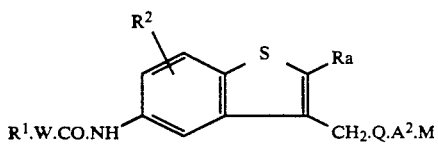

imidazole derivatives of formula IId,

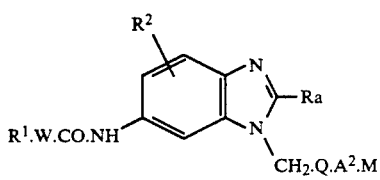

benzotriazole derivatives of formula IIf,

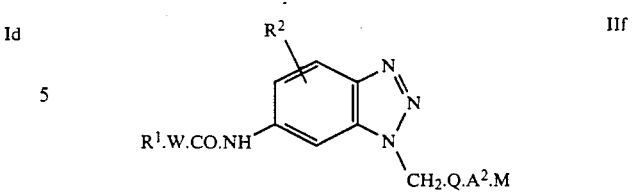

and
indazole derivatives of formula IIg;

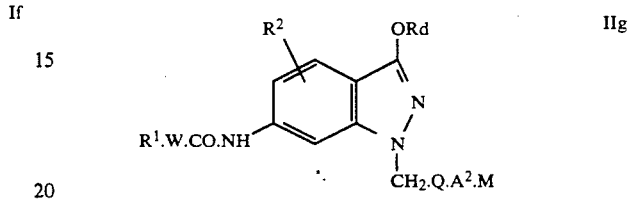

or a pharmaceutically acceptable salt thereof.

6. A compound as claimed in claim 4 wherein
$A^1$ is methylene;
$A^2$ is a direct link to M;
Q is p-phenylene optionally substituted by methoxy;
M is selected from the group consisting of carboxy, 1-tetrazol-5-yl, and a radical of the formula $-CO.NH.SO_2R^4$ wherein $R^4$ is phenyl, optionally substituted as defined for $R^3$.

7. A compound as claimed in any one of claims 1-3, wherein $R^1.L-$ is attached to the benzene moiety of formula I in such a way that it bears a meta-relationship t the group X but does not bear an ortho-relationship to the group Z.

8. A compound as claimed in claim 5 selected from the group consisting of
compounds of formula IIg wherein $R^1.L-$ is $R^1.W.CO.NH-$ wherein $R^1.W-$ is cyclopentyloxy, M is carboxy or $-CO.NH.SO_2R^4$ wherein $R^4$ is phenyl, and Rd is methyl; and
compounds of formula IIg wherein $R^1.L-$ is $R^1.W.CO.NH-$ wherein $R^1$ is cyclopentylmethyl, W is a direct linkage, M is carboxy or $-CO.NH.SO_2R^4$ wherein $R^4$ is 2-methylphenyl, and Rd is N-ethylcarbamoylmethyl.

9. A compound as claimed in claim 1 wherein said compound is selected from the group consisting of
N-[4-[5-(cyclopentyloxycarbonyl)aminobenzo[b]thien-3-ylmethyl]-3-methoxybenzoyl]benzenesulphonamide,
N-[4-[6-(2-cyclopentylacetamido)benzimidazol-1-ylmethyl]-3-methoxybenzoyl]benzenesulphonamide,
N-[4-[6-(cyclopentyloxycarbonyl)amino-3-methoxyindazol-1-ylmethyl]-3-methoxybenzoyl]benzenesulphonamide,
N-[4-[6-(2-cyclopentylacetamido)benzotriazol-1-ylmethyl]-3-methoxybenzoyl]benzenesulphonamide,
N-[4-[6-(2-cyclopentylacetamido)-3-(N-ethylcarbamoylmethoxy)indazol-1-ylmethyl]-3-methoxybenzoyl]-2-methylbenzenesulphonamide, and
N-[4-[6-(cyclopentyloxycarbonyl)aminobenzimidazol-1-ylmethyl]-3-methoxybenzoyl]benzenesulphonamide;
or a pharmaceutically acceptable salt thereof.

10. A salt of a compound as claimed in claim 1.
11. A compound of formula III

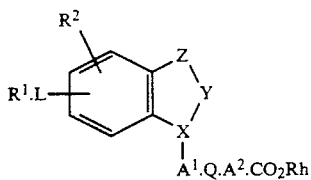

III

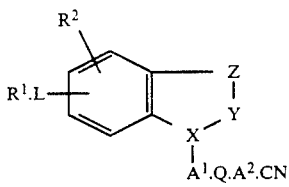

VIII wherein the groups and substituents have the meanings as defined in claim 1.

wherein Rh is selected from the group consisting of (a) (1-6C)alkyl optionally bearing an acetoxy, (1-4C)-alkoxy or (1-4C)alkylthio group; (b) phenyl; and (c) benzyl; and wherein the other groups and substituents have the meaning as defined in claim 1.

12. A compound of formula VII

13. A pharmaceutical composition having leukotriene antagonist properties comprising a pharmaceutically effective amount of a compound as claimed in claim 1 and a non-toxic pharmaceutically-acceptable diluent or carrier.

14. A composition as claimed in claim 13 wherein said composition is in the form of a liquid or powdered aerosol.

15. A method for antagonizing one or more of the actions of leukotrienes in a living mammal comprising administering to said mammal an effective amount of a compound claimed in claim 1.

* * * * *